(12) United States Patent
Erickson et al.

(10) Patent No.: US 7,388,091 B2
(45) Date of Patent: Jun. 17, 2008

(54) **HARVEST-INDUCIBLE GENES FROM ALFALFA (*MEDICAGO SATIVA*) AND METHODS OF USE THEREOF**

(75) Inventors: Larry Erickson, Guelph (CA); Jian Zhang, Guelph (CA)

(73) Assignee: University of Guelph, Guelph (CA)

( * ) Notice: Subject to any disclaimer, the term of this patent is extended or adjusted under 35 U.S.C. 154(b) by 135 days.

(21) Appl. No.: 10/519,811

(22) PCT Filed: Jun. 27, 2003

(86) PCT No.: PCT/CA03/00964

§ 371 (c)(1),
(2), (4) Date: Jul. 28, 2005

(87) PCT Pub. No.: WO2004/002216

PCT Pub. Date: Jan. 8, 2004

(65) Prior Publication Data

US 2006/0168676 A1     Jul. 27, 2006

Related U.S. Application Data

(60) Provisional application No. 60/392,444, filed on Jun. 28, 2002.

(51) Int. Cl.
*C07H 21/04* (2006.01)
*C12N 15/82* (2006.01)
*A01H 5/00* (2006.01)

(52) U.S. Cl. .................. 536/24.1; 435/320.1; 800/298; 800/287; 800/288

(58) Field of Classification Search ...................... None
See application file for complete search history.

(56) References Cited

U.S. PATENT DOCUMENTS

| | | |
|---|---|---|
| 4,693,976 A | 9/1987 | Schilperoort et al. |
| 4,743,548 A | 5/1988 | Crossway et al. |
| 4,940,835 A | 7/1990 | Shah et al. |
| 4,943,674 A | 7/1990 | Houck et al. |
| 5,013,660 A | 5/1991 | Kasuya et al. |
| 5,116,750 A | 5/1992 | Gelfand et al. |
| 5,120,657 A | 6/1992 | McCabe et al. |
| 5,149,645 A | 9/1992 | Hoekema et al. |
| 5,179,022 A | 1/1993 | Sanford et al. |
| 5,202,422 A | 4/1993 | Hiatt et al. |
| 5,302,523 A | 4/1994 | Coffee et al. |
| 5,371,015 A | 12/1994 | Sanford et al. |
| 5,436,393 A | 7/1995 | Rocha-Sosa et al. |
| 5,453,367 A | 9/1995 | Paszkowski et al. |
| 5,464,765 A | 11/1995 | Coffee et al. |
| 5,484,719 A | 1/1996 | Lam et al. |
| 5,487,991 A | 1/1996 | Vandekerckhove et al. |
| 5,504,200 A | 4/1996 | Hall et al. |
| 5,530,194 A | 6/1996 | Knauf et al. |
| 5,565,340 A | 10/1996 | Chenchik et al. |
| 5,591,616 A | 1/1997 | Hiei et al. |
| 5,612,487 A | 3/1997 | Lam et al. |
| 5,639,947 A | 6/1997 | Hiatt et al. |
| 5,648,477 A | 7/1997 | Leemans et al. |
| 5,654,184 A | 8/1997 | Curtiss, III et al. |
| 5,670,349 A * | 9/1997 | Cramer et al. ............. 435/69.1 |
| 5,679,880 A | 10/1997 | Curtiss, III et al. |
| 5,689,056 A | 11/1997 | Cramer et al. |
| 5,693,512 A | 12/1997 | Finer et al. |
| 5,714,474 A | 2/1998 | Van Ooijen et al. |
| 5,716,802 A | 2/1998 | Sijmons et al. |
| 5,723,757 A | 3/1998 | Rocha-Sosa et al. |
| 5,763,748 A | 6/1998 | Sijmons et al. |
| 5,767,379 A | 6/1998 | Baszczynski et al. |
| 5,777,200 A | 7/1998 | Ryals et al. |
| 5,792,922 A | 8/1998 | Moloney |
| 5,804,694 A | 9/1998 | Bruce et al. |
| 5,824,870 A | 10/1998 | Baszczynski et al. |
| 5,859,327 A | 1/1999 | Dev et al. |
| 5,865,796 A | 2/1999 | McCabe |
| 5,905,186 A | 5/1999 | Thomas et al. |
| 5,914,123 A | 6/1999 | Arntzen et al. |
| 5,929,304 A | 7/1999 | Radin et al. |
| 5,948,682 A | 9/1999 | Moloney |
| 5,959,177 A | 9/1999 | Hein et al. |
| 5,981,835 A | 11/1999 | Austin-Phillips et al. |
| 6,002,070 A | 12/1999 | D'Halluin et al. |
| 6,034,298 A | 3/2000 | Lam et al. |

(Continued)

FOREIGN PATENT DOCUMENTS

EP         0 120 516 A2      10/1984

(Continued)

OTHER PUBLICATIONS

Donald et al. Mutation of either G box or I box sequences profoundly affects expression from *Arabidopsis* rbcs-1A promoter. (1990) The EMBO Journal, vol. 9, pp. 1717-1726.*

Benfey et al. The cauliflower mosaic virus 35S promoter: combinatorial regulation of transcription in plants. (1990) Science, vol. 250, pp. 959-966.*

Kim et al. A 20 nucleotide upstream element is essential for the nopaline synthase (nos) promoter activity. (1994) PMB, vol. 24, pp. 105-117.*

Churchill et al., "Structure-Activity Relationships of Abscisic Acid Analogs Based on the Induction of Freezing Tolerance in Bromegrass (*Bromus inermis leyss*) Cell Cultures", Plant Physiology (1992); 100: 2024-2029.

Volenec et al., "Molecular Analysis of Alfalfa Root Vegetative Storage Proteins", Molecular and Cellular Technologies for Forage Improvement (1998); CSSA Special Publication No. 26, Chapter 6: 59-73.

(Continued)

*Primary Examiner*—Ashwin D. Mehta
*Assistant Examiner*—Cathy Kingdon Worley
(74) *Attorney, Agent, or Firm*—Merchant & Gould P.C.

(57) ABSTRACT

The present invention relates to novel inducible genes from alfalfa. These genes are highly induced following mechanical harvesting or wounding of alfalfa. The genes are useful for inducible production of heterologous proteins following harvesting.

9 Claims, 13 Drawing Sheets

U.S. PATENT DOCUMENTS

| | | | |
|---|---|---|---|
| 6,046,037 A | 4/2000 | Hiatt et al. | |
| 6,048,730 A | 4/2000 | Waldron | |
| 6,136,320 A | 10/2000 | Arntzen et al. | |
| 6,650,307 B1 | 11/2003 | Toda et al. | |
| 6,783,394 B1 | 8/2004 | Holliday | |

FOREIGN PATENT DOCUMENTS

| | | |
|---|---|---|
| EP | 0 120 516 B1 | 10/1984 |
| EP | 0 131 320 | 1/1985 |
| WO | 97/02900 | 1/1997 |
| WO | 99/37784 | 7/1999 |
| WO | 99/67401 | 12/1999 |
| WO | 00/31251 | 6/2000 |
| WO | 01/73090 | 10/2001 |

OTHER PUBLICATIONS

Walker-Simmons et al., "Optically Pure Abscisic Acid Analogs-Tools for Relating Germination Inhibition and Gene Expression in Wheat Embryos", Plant Physiology (1992); 99: 501-507.

Ferullo et al., "Post-Harvest Alteration of In Vitro Translatable mRNA Population in Alfalfa (*Medicago sativa l.*)", Crop Science (1996); 36: 1011-1016.

Matz et al. "Different strategies of differential display: areas of application", Nucleic Acids Research (1998); 26: 5537-5543.

Kuhn, "From Library Screening to Microarray Technology: Strategies to Determine Gene Expression Profiles and to Identify Differentially Regulated Genes in Plants", Annals of Botany (2001); 87: 139-155.

Iwasaki et al., "Identification of a *cis*-regulatory region of a gene in *Arabidopsis thaliana* whose induction by dehydration is mediated by abscisic acid and requires protein synthesis," Mol Gen Genet (1995) 247: 391-398.

\* cited by examiner

```
acgcgtggtc gacggcccgg gctggtacta aagtattact attaccaaat ttttaggacc    60
ccacccatga caccattgct atatttcaat tggggaaaat attgctataa agttactgta   120
gtaactttta gaagaaggtt ttttttttaa ggattttaga ggaaggttag caacacacat   180
gcactttaaa tatacatttt ttcttataaa gttttgtat cgagttgaga aatcatatat    240
atactcataa atcatgtgga tttcatataa tttaatagaa cacataaatt ttaaccgaga   300
aataaagtgt tgcaaatata tgttaaaaga gtacgttgtt aacattattt taatttcttt   360
tattcaatcc acactttgag tcatggactg ctatactaat tcattttgtt tttcgcaacc   420
taattagaga ttgtccagat acaaagagga gtaacctaat aaataaatat taaaatattc   480
accaacggcc tcagtaagct acttgagcta aacaatgaga tttccaaata aggtaggtcc   540
ttcccaagtt c[tata]aatag catccctcac catgtcataa accgcatcac aagt[tatata]  600
CTGTATTCAT ACTATACACT TATCCTTTCA TTTACTTCTT GCATATTGAT CCTTGTTATC   660
TTGATATATA TATCATGGGTGTTTTTACTTTCAATGATGAACATGTCTCAACCGTGGCTC      720
           M  G  V  F  T  F  N  D  E  H  V  S  T  V  A
CAGCTAAACTCTACAAGGCTCTTGCAAAAGATGCTGATGAAATCGTCCCAAAGGTGATTT       780
 P  A  K  L  Y  K  A  L  A  K  D  A  D  E  I  V  P  K  V  I
CTGCTGCCCAAAGTGTTGAAATTGTTGAAGGAAATGGAGGACCCGGAACTATTAAGAAGC       840
  S  A  A  Q  S  V  E  I  V  E  G  N  G  G  P  G  T  I  K  K
TATCCATTGTTGAAGATGGCAAAACCAACTTTGTGCTACACAAATTAGATTCAGTGGATG       900
 L  S  I  V  E  D  G  K  T  N  F  V  L  H  K  L  D  S  V  D
AGGCAAACTTTGGATATAACTACAGCTTAGTGGGAGGAACAGGGTTGGATGAAAGTTTAG       960
  E  A  N  F  G  Y  N  Y  S  L  V  G  G  T  G  L  D  E  S  L
AGAAAGTTGAATTTGAGACAAAAATTGTTGCTGGCTCTGATGGTGGATCCATTGTTAAGA      1020
 E  K  V  E  F  E  T  K  I  V  A  G  S  D  G  G  S  I  V  K
TTTCAGTGAAATACCATACCAAAGGTGATGCAACTCTATCTGAAGCAGTACGTGAGGAGA      1080
  I  S  V  K  Y  H  T  K  G  D  A  T  L  S  E  A  V  R  E  E
CTAAGGCCAAAGGAACTGGACTTATCAAGGCCATTGAGGGCTACGTTTTAGCAAACCCTA      1140
 T  K  A  K  G  T  G  L  I  K  A  I  E  G  Y  V  L  A  N  P
ATTACTAGCC AATTAAACCC TATTGAGGAC TTTAATTTGG GTTGTGTTGT TCATGCGAA  1200
 N  Y  *
TAATAATTAA AGTTTATGAT GCGGTTGAAG TGTGTTGAGT ATACATCAAG GTCTTTGGCT 1260
CGTACATGTG TGTTGGCTTT GTTGGATGTT GTGAGGTTTG AGTGCTATTT TGGGTGTTTA 1320
AAAACAAAAA CCTATGTTGT GTTGGTGATA AGGTTTTGCA CCATCTGTAT TATGCAATAA 1380
ATAATGCAAA AGAATTTTAT CGCGAAAAAA AAAAAAAAAA AAAA                  1424
```

FIG. 8

```
cagaacccccg anaggctggt gctagtatgg cttcgttgta atacgactca ctatagggcg  60
cgcgtggtcg acggcccggg ctggtatcag cgagtaacga ttcatcatat ctcacactag 120
ggatgaatga tttattattg agtttatgaa tttgaactat tacttctaat ttctaaatga 180
agacatttaa gtaaaagatt aaaatattct agtttcaaat attttggatt ttagaattta 240
aatttaatct ttaaaaaaaa attaaattta aagaagataa aaagggagaa aataaataga 300
tgaatataat ttgtaaacat gaagaccttta tctccagtaa aaaaacatat ggaccttatc 360
tttttgaggt aggaaggatc tacgcgggga acctcttcct gactgtgaac cccgtatgca 420
gaggcagaga cagagagtAT GGCCTCCACA CTCAGTCTTG TCAAGCTTCC CATTCTTTCA 480
AGCATCAAGA CACGCCAATC AACCTCAAAA CATGTTGTTC CACTTCCATC CAAATTCAAT 540
ATTGTCCCTC CCACCCCACT AAAGTTTTCA TTAGATCATC AAATTAATAT CAAACAAACT 600
TCTCTTCTAT CCCTCACAGC AATCACATTT CCATTCTTAT TGGATACCAA ggcaagcaag 660
caagcaagca tcctattcta ttctattctt tcatccatat ctttactctt ttgttttcta 720
accaatccat gatatgaatg ttgttgaaac aggatgcact tgctgttggt ggAGAGTTTG 780
GGATATTTGA AGGAAGAACA TTTGCTCTCA TTCACCCCAT TGTGTTGGGT GGTTTGTTCT 840
TCTATACTCT ATATGCTGGC TATTTGGGGT GGCAATGGCG CCGAGTTAGG ACTATTCAAA 900
ATGATATTAA TGAGCTCAAG AAACAACTCA AACCTGCACC GGTCGCCCCT GATGGTAAAG 960
CACTTGAAAC TTCACCGCCA TCACCTGTTG AACTTCAAAT CCAGAAACTT ACTGAGGAGA 1020
GGAAAGAGCT TATCAAAGGT TCATACAGGG ATAAACACTT TAATGCTGGA TCCATACTTC 1080
TAGGATTTGG TGTCTTTGAG GCTGTTGGTG TGAGGACTCA ACACATGGTT AAGGACAGGA 1140
AAGCTATTTC CAGGTCCACA TTTATTTGCA GGAGCAGGCA TTACCGTCTT ATGGGCACTG 1200
GCAGCAGCTC TAGTACCACC GATGCAGAAA GGCAGTGAaa cagccagaaa tcttcacatt 1260
gctctgaata cattgaatgt tcttctcttt gtgtggcaga ttcccactgg acttgatatt 1320
gtatggaaag tgtttgagtt cacaaaatgg ccttgaatgt atgattctca tatgtaagta 1380
agttcccagg tatttttactt tcaaatcagt atttggcaat atcaataaat gcaaaatttg 1440
ctattctgca ttttcaaaaa aaaaaaaaaa aaaaaaaaaa aa 1482
```

FIG. 9

```
  1  aaatacaaag gtgaccttat tttgcaaata atccatgcat ggaaatgcat catccttttg
 61  aaaatgggtt tatctgaatt cttaa gttacgtgaa aattt aatacatttc attttagata
                                 ABRE cis-acting element
121  aatttattat taaaattcac acttagatgg cctaaaaatt aacacttatt tttaacaatt
181  caaataaaat atacgacgaa atgagtgtaa tttagttggt taagcatcgt caaagcttgg
241  agagaaagat catagtttga tctttgaaaa ctatactatt gaaaagggtg aagatatcta
301  acctccaaca aaatttattt gatagtcgat tcaaattatc aaaatttgga aaatattttg
361  taaattgtta agttgggaaa aatatgttaa ttttcaaatt accatttgca cattttccta
421  atctcaaatc acatttaagg gatgttgact actttcgttt tgtacaaatc tttacaattt
481  taacatttat aaaatgtgtt ttggtagata aaagtgtga gtattcttta taagagattg
541  tgtttttctt ttgtttttaac ttataaaata aatatatatt ttatttttatt ttaacgtgag
601  attgtaagaa ttcattataa gattatgtca ttccctcaaa agaaaattag atgatgtcat
661  tttcataact cattttctat aaatacagaa aatcctcaaa aatgaaaaac ctcggtcaaa
721  aaataaaaga aaaacatcaa tagtggactg gcccacactc attgctttgc tttagtatga
781  gaaagtagac ctcaccaacc acgaaccgga cgccgaccgg ttca accaaa catcacacca
                                                     CAAT-BOX
841  attttcctaa accataccgg ttttccctc cct tatata a ccatcctctc ccctcttctc
                                       TATA-BOX
901  taaccaagct tcattcaact cttcaacaca tatcagaaaC AGAAAAAAGA AGCAAAACAT
961  TCCAAGAATT TAACAATGGCAACCAACGAAGATCAAAAGCAAACTGAATCTGGAAGACAT
                  M  A  T  N  E  D  Q  K  Q  T  E  S  G  R  H
1021 CAAGAAGTTGGTCACAAGAGTCTTTTACAAAGTGATGCTCTTTACCAGTATATTCTAGAG
      Q  E  V  G  H  K  S  L  L  Q  S  D  A  L  Y  Q  Y  I  L  E
1081 ACCAGTGTCTTCCCAAGAGAACATGAAGCCATGAAAGAGTTGAGAGAGGTCACAGCAAAA
      T  S  V  F  P  R  E  H  E  A  M  K  E  L  R  E  V  T  A  K
1141 CACCCATGGAACATCATGACAACCTCTGCAGATGAAGGACAATTTTTGAGCATGCTCCTT
      H  P  W  N  I  M  T  T  S  A  D  E  G  Q  F  L  S  M  L  L
1201 AAACTTATCAATGCTAAGAATACCATGGAAATTGGTGTCTACACTGGCTACTCCCTCCTT
      K  L  I  N  A  K  N  T  M  E  I  G  V  Y  T  G  Y  S  L  L
1261 GCCACTGCCCTAGCTATTCCTGAAGATGGAAAGATTTTGGCTATGGACATTAACAAAGAA
      A  T  A  L  A  I  P  E  D  G  K  I  L  A  M  D  I  N  K  E
1321 AATTACGAATTGGGTCTACCTGTAATTAAAAAAGCTGGTGTTGATCACAAAATTGATTTC
      N  Y  E  L  G  L  P  V  I  K  K  A  G  V  D  H  K  I  D  F
1381 AGAGAAGGTCCAGCTCTTCCAGTTCTTGATGAAATGATCAAAGACGAAAAGAATCATGGT
      R  E  G  P  A  L  P  V  L  D  E  M  I  K  D  E  K  N  H  G
1441 AGCTACGATTTCATTTTTGTGGATGCTGACAAAGACAATTACCTCAACTACCATAAGAGG
      S  Y  D  F  I  F  V  D  A  D  K  D  N  Y  L  N  Y  H  K  R
1501 TTAATTGATCTTGTTAAAGTGGGAGGTGTGATCGGGTACGACAACACCTTATGGAATGGA
      L  I  D  L  V  K  V  G  G  V  I  G  Y  D  N  T  L  W  N  G
1561 TCTGTGGTTGCACCCCCTGATGCTCCATTGAGGAAGTATGTTAGGTACTATAGAGATTTT
      S  V  V  A  P  P  D  A  P  L  R  K  Y  V  R  Y  Y  R  D  F
1621 GTTTTGGAGCTTAACAAGGCTTTGGCTGTGGACCCTAGGATTGAAATATGTATGCTTCCT
      V  L  E  L  N  K  A  L  A  V  D  P  R  I  E  I  C  M  L  P
1681 GTTGGTGATGGAATCACTATCTGCCGTAGGATCAAGTAA TTGGTTTGCATGTGCACTATA
      V  G  D  G  I  T  I  C  R  R  I  K  *
1741 TCATGTAATGCACTGCTCCACATTATTGATCATTATTGTGTGGAAGCTACAGAGCATTTA 1801 AAAGTCTTCAAGCCTTCTTGTCTTTTGTTATTTTTCTTCAACATATTTGTGGTTGTAATT
1861 TTCTCTTGTC ATTGATATTG AAACTTCGAA TAATTGAAAG TTATAT
```

FIG. 10

HARVEST-INDUCIBLE GENES FROM ALFALFA (*MEDICAGO SATIVA*) AND METHODS OF USE THEREOF

"This application is the National Stage of Application PCT/CA2003/000964 filed Jun. 27, 2003, which is the International Application of U.S. Provisional Application No. 60/392,444 filed Jun. 28, 2002, and which application(s) are incorporated herein by reference."

The present invention relates to recombinant protein production in plants. More particularly, the present invention relates to novel inducible genes that are expressed upon harvest, methods for isolating such genes, and methods for using these genes or components therefrom.

BACKGROUND OF THE INVENTION

The mass production of recombinant molecules of commercial value is a technical area of increasing complexity and interest. Many different organisms have been considered as hosts for foreign protein expression including single-cell organisms such as bacteria and yeast, cell cultures of animals, fungi and plants, and whole organisms such as plants, insects, fungi and transgenic animals. In general, each particular organism has unique characteristics that may offer advantages for production of specific proteins of interest. Alternatively the specificity of certain protein production platforms may limit utility for widespread applications. Thus, numerous molecular farming systems have been developed as a means to produce proteins of commercial interest.

Of particular interest to the subject matter of the present invention is the expression of heterologous proteins in plant cells. Numerous foreign proteins have been expressed in whole plants and selected plant organs. Plants can offer a highly effective and economical means to produce recombinant proteins as they can be grown on a large scale with modest cost inputs and most commercially important species can now be transformed.

In order to optimize protein production and recovery, a number of factors need to be considered. These include the levels of recombinant protein production, the temporal aspects of recombinant protein production, and the stability of the final product within the plant cell. The level of protein production must be sufficient to allow accumulation of the product in quantities that are commercially valuable and can be conveniently isolated. In many instances, it may be desired that the temporal expression of the product coincide with the period when the crop is harvested or collected. In addition, it may be required that the protein stably accumulate to appreciable levels, or be induced to quickly accumulate to appreciable levels if the product is intrinsically unstable.

The production of heterologous proteins in plants has been achieved using a variety of approaches. U.S. Pat. Nos. 6,650,307, 5,716,802, 5,763,748 disclose recombinant protein production using transcriptional fusions to a constitutive plant promoter. Production of heterologous proteins in seed (U.S. Pat. Nos. 5,504,200; 5,530,194; 6,905,186; 5,792,922; 5,948,682), fruit (U.S. Pat. Nos. 6,783,394; 4,943,674) or storage organs such as tubers (U.S. Pat. Nos. 5,436,393, 5,723,757) have also been described.

A disadvantage of constitutive expression systems is that constitutive expression of a protein may lead to toxic effects with regards to plant growth. Furthermore, it is difficult to predict what interactions a foreign protein may have with other plant proteins, such as enzymes or receptors, plant membranes, such as those of the endoplasmic reticulum, Golgi apparatus, vacuole and plasmalemma, or the host of other molecules critical to the growth and development of the plant. Another potential disadvantage of a constitutive or non-inducible promoter is the metabolic cost of synthesizing the transgenic protein in all tissues at all stages of growth. If the only tissue to be harvested is the leaves, for example, it is inefficient and wasteful for the plant to produce the foreign protein in other tissues. Alternatively, if the transgene encoded protein is labile or unstable, then production of the protein, constitutively, throughout the growth of the plant is inefficient.

Inducible systems allow the expression of an introduced gene to take place at a desired time in the development of a plant, under specific circumstances or in specific tissues. For example, leaf-specific promoters or promoters induced in the leaves by some treatment would restrict synthesis to only the harvested tissue. In addition, an induced foreign gene is potentially less likely to undergo gene silencing than a transgene controlled by a constitutive or tissue specific promoter. Furthermore, inducible transgene systems offer a method of biological containment since the foreign protein is not present in the crop until the application of the inducing treatment, at which time the crop is harvested. Containment of a protein produced from a foreign gene is as, or more, important than containment of the gene as the protein is the biologically active component.

Gene expression in response to plant wounding is another potential source of an inducible system. U.S. Pat. Nos. 5,689,056, 5,670,349, 5,929,304, and U.S. Pat. No. 5,777,200 disclose the use of regulatory elements from wound inducible genes for the induction of heterologous protein synthesis in plants. However, the value of these wound-inducible promoters may be limited since wounding of the plant also induce other genes, such as proteases, that can negatively impact the production of the recombinant protein. It is also not clear that these regulatory elements provide sufficient levels of expression to cause accumulation of the recombinant protein to substantial levels, especially when the response is localized to the site of wounding (e.g. HMG2 promoter, U.S. Pat. No. 5,689,056). Although the expression levels with such promoters can be enhanced by applying more extensive wounding treatments or chemical inducers such as methyl jasmonate, this entails additional costs.

Thus, although promoters involved in inducible systems can provide powerful tools for control of transgenes in plants, many obstacles are faced in utilizing these regulatory elements. Inducible promoter systems must enable the precise timing and location of expression of such transgenes in order to be commercially useful. In this regard, regulatory elements that can be induced under precise conditions amenable to cultivation practices are desired. More particularly, there is a need for regulatory elements that are induced, specifically, during harvesting conditions.

Volenec et al. ("Molecular analysis of alfalfa root vegetative storage proteins" pp59-73 in Molecular and Cellular Technologies for Forage Improvement, CSSA Spec Publ. No. 26, 1998) have characterized the changes that ensue in root tissue following harvest and shoot regrowth of alfalfa (*Medicago sativa* L.). However, no specific regulatory elements were identified or characterized in any manner.

Ferullo et al (Crop. Sci. 1996 36, 1011-1016) disclose proteins that are specific to harvesting conditions of alfalfa. However the structure or function of these proteins was not characterized and is unknown; moreover, there is no indication of the nature of the genes expressed in harvested shoot tissue of alfalfa during harvesting. Furthermore, there is no suggestion as to the use of regulatory elements associated with these genes for induction of heterologous gene expression in plants in a harvest-inducible manner.

Coupe et al. (WO 00/31251) disclose the characterization of a promoter from asparagine synthetase and its use in post harvest gene expression.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to recombinant protein production in plants. More particularly, the present invention relates to novel inducible genes that are expressed upon harvest, methods for isolating such genes, as well as methods for using these genes.

The present invention provides a method (A) for isolating a harvest-inducible DNA sequence comprising:

i) constructing one or more first cDNA libraries comprising cDNA sequences expressed in harvested tissue;

ii) preparing one or more second cDNA libraries comprising cDNA sequences expressed in tissues of an intact plant prior to harvest; and iii) identifying harvest-inducible cDNA sequences. The expression of the harvest-inducible cDNA sequences may be analyzed to determine inducibility of the harvest-inducible cDNA sequences upon harvesting.

An example of identifying harvest-induced cDNA sequences (step iii)) include subtractive hybridization of the first cDNA library with an excess of the second cDNA library, however, other methods may also be used as known in the art.

The present invention also relates to an isolated harvest-inducible cDNA sequence obtained according to the above method (A).

The present invention embraces an isolated harvest-inducible cDNA sequence selected from the group consisting of:

i) SEQ ID NO:1, a complement thereof, a fragment of SEQ ID NO:1, a complement of a fragment of SEQ ID NO:1, a nucleic acid that hybridizes to SEQ ID NO:1 under stringent hybridization conditions, a nucleic acid that hybridizes to a complement of SEQ ID NO:1 under stringent hybridization conditions, a nucleic acid that hybridizes to a fragment of SEQ ID NO:1 under stringent hybridization conditions, or a nucleic acid that hybridizes to a complement of fragment of SEQ ID NO:1 under stringent hybridization conditions;

ii) SEQ ID NO:2, a complement thereof, a fragment of SEQ ID NO:2, a complement of a fragment of SEQ ID NO:2, a nucleic acid that hybridizes to SEQ ID NO:2 under stringent hybridization conditions, a nucleic acid that hybridizes to a complement of SEQ ID NO:2 under stringent hybridization conditions, a nucleic acid that hybridizes to a fragment of SEQ ID NO:2 under stringent hybridization conditions, or a nucleic acid that hybridizes to a complement of fragment of SEQ ID NO:2 under stringent hybridization conditions; and iii) SEQ ID NO:3, a complement thereof, a fragment of SEQ ID NO:3, a complement of a fragment of SEQ ID NO:3, a nucleic acid that hybridizes to SEQ ID NO:3 under stringent hybridization conditions, a nucleic acid that hybridizes to a complement of SEQ ID NO:3 under stringent hybridization conditions, a nucleic acid that hybridizes to a fragment of SEQ ID NO:3 under stringent hybridization conditions, or a nucleic acid that hybridizes to a complement of fragment of SEQ ID NO:3 under stringent hybridization conditions, the stringent hybridization conditions comprising, hybridization overnight (12-24 hrs) at 42° C. in the presence of 50% formamide, followed by washing, or 5×SSC at about 65° C. for about 12 to about 24 hours, followed by washing in 0.1×SSC at 65° C. for about one hour.

Also provided in this invention is a method (B) for isolating a harvest inducible regulatory element comprising, i) identifying genomic DNA sequences 3' and 5' corresponding to the harvest-inducible cDNA identified using method (A); and ii) analyzing the genomic DNA, and identifying the harvest-inducible regulatory element.

This method (B) may further comprise a step of:

iii) testing the harvest-inducible regulatory region within a transgenic plant or plant cell.

The present invention also provides a harvest-inducible regulatory element obtained using the method (B).

The present invention also pertains to a harvest-inducible regulatory element selected from the group consisting of:

i) SEQ ID NO:4, a complement thereof, a fragment of SEQ ID NO:4, a complement of a fragment of SEQ ID NO:4, a nucleic acid that hybridizes to SEQ ID NO:4 under stringent hybridization conditions, a nucleic acid that hybridizes to a complement of SEQ ID NO:4 under stringent hybridization conditions, a nucleic acid that hybridizes to a fragment of SEQ ID NO:4 under stringent hybridization conditions, or a nucleic acid that hybridizes to a complement of fragment of SEQ ID NO:4 under stringent hybridization conditions;

ii) SEQ ID NO:5, a complement thereof, a fragment of SEQ ID NO:5, a complement of a fragment of SEQ ID NO:5, a nucleic acid that hybridizes to SEQ ID NO:5 under stringent hybridization conditions, a nucleic acid that hybridizes to a complement of SEQ ID NO:5 under stringent hybridization conditions, a nucleic acid that hybridizes to a fragment of SEQ ID NO:5 under stringent hybridization conditions, or a nucleic acid that hybridizes to a complement of fragment of SEQ ID NO:5 under stringent hybridization conditions; and iii) SEQ ID NO:6, a complement thereof, a fragment of SEQ ID NO:6, a complement of a fragment of SEQ ID NO:6, a nucleic acid that hybridizes to SEQ ID NO:6 under stringent hybridization conditions, a nucleic acid that hybridizes to a complement of SEQ ID NO:6 under stringent hybridization conditions, a nucleic acid that hybridizes to a fragment of SEQ ID NO:6 under stringent hybridization conditions, or a nucleic acid that hybridizes to a complement of fragment of SEQ ID NO:6 under stringent hybridization conditions, the stringent hybridization conditions comprising, hybridization overnight (12-24 hrs) at 42° C. in the presence of 50% formamide, followed by washing, or 5×SSC at about 65° C. for about 12 to about 24 hours, followed by washing in 0.1×SSC at 65° C. for about one hour, wherein the regulatory element exhibits harvest-inducible activity.

Also provided in the present invention is a construct comprising the harvest-inducible regulatory element as just defined, operably linked with a heterologous nucleotide sequence of interest and a terminator region. The present invention also embraces a vector comprising the DNA construct as just defined. Furthermore, this invention pertains to a plant, plant tissue, plant seed, plant cell, or progeny therefrom, comprising the construct as just defined.

The present invention relates to a construct comprising a heterologous nucleotide sequence operably linked to said harvest-inducible regulatory element defined above, where the harvest-inducible regulatory element further comprises a nucleotide sequence encoding a harvest-inducible protein or fragment thereof. The present invention also embraces a vector comprising the DNA construct as just defined. Furthermore, this invention pertains to a plant, plant tissue, plant seed, plant cell, or progeny therefrom, comprising the construct as just defined The present invention also provides a method (C) for production of a heterologous protein into a plant comprising:

i) introducing a construct comprising a harvest-inducible regulatory element operably linked with a heterologous nucleotide sequence of interest and a terminator region, to the plant to obtain a transformed plant, where the harvest-inducible regulatory element is selected from the group consisting of:

SEQ ID NO:4, or a fragment thereof;
SEQ ID NO:5, or a fragment thereof;
SEQ ID NO:6, of a fragment thereof;
a nucleic acid that hybridizes to SEQ ID NO:4, 5, 6, or a complement of SEQ ID NO:4, 5, 6 under stringent hybridization conditions; and
a nucleic acid that hybridizes to a fragment of SEQ ID NO:4, 5, 6, or a complement of SEQ ID NO:4, 5, 6 under stringent hybridization conditions, the stringent hybridization conditions comprising, hybridization overnight (12-24 hrs) at 42° C. in the presence of 50% formamide, followed by washing, or 5×SSC at about 65° C. for about 12 to about 24 hours, followed by washing in 0.1×SSC at 65° C. for about one hour;

ii) growing the transformed plant; and
iii) harvesting the transformed plant thereby inducing expression of the heterologous protein.

The step of harvesting (step iii) may be followed by:
iv) isolating the heterologous protein from the transformed plant.

Furthermore, the step of isolating (step iv)) may be followed by a step of purification of the heterologous protein.

The present invention also pertains to a method (D) for production of a heterologous protein comprising, i) providing a plant transformed with a construct comprising a harvest-inducible regulatory element operably linked with a heterologous nucleotide sequence of interest and a terminator region, where the harvest-inducible regulatory element is selected from the group consisting of SEQ ID NO:4, or a fragment thereof;
SEQ ID NO:5, or a fragment thereof;
SEQ ID NO:6, of a fragment thereof;
a nucleic acid that hybridizes to SEQ ID NO:4, 5, 6, or a complement of SEQ ID NO:4, 5, 6 under stringent hybridization conditions; and
a nucleic acid that hybridizes to a fragment of SEQ ID NO:4, 5, 6, or a complement of SEQ ID NO:4, 5, 6 under stringent hybridization conditions, the stringent hybridization conditions comprising, hybridization overnight (12-24 hrs) at 42° C. in the presence of 50% formamide, followed by washing, or 5×SSC at about 65° C. for about 12 to about 24 hours, followed by washing in 0.1×SSC at 65° C. for about one hour, and the harvest-inducible regulatory element further comprises a nucleotide sequence encoding a harvest-inducible protein or fragment thereof;

ii) growing the transformed plant; and
iii) harvesting the transformed plant to induce expression of the heterologous protein.

The step of harvesting (step iii) may be followed by:
iv) isolating the heterologous protein from the transformed plant.

Furthermore, the step of isolating (step iv)) may be followed by a step of purification of the heterologous protein.

The harvest-inducible regulatory elements can be used to control the expression of a heterologous DNA sequence, such that the heterologous DNA sequence is only expressed in response to harvesting, thus providing a convenient system for the production of novel proteins. Accordingly, another aspect of the present invention is directed to DNA constructs comprising a harvest-inducible regulatory element operably linked with a heterologous nucleotide sequence of interest and a terminator region.

In order to enhance translation, stability or recovery of the heterologous or foreign protein, the nucleotide sequence encoding the heterologous protein can be operably linked to a harvest-inducible gene encoding a portion of a harvest-inducible protein and its corresponding harvest-inducible regulatory element. Accordingly, another aspect of the present invention relates to a DNA construct comprising a heterologous nucleotide sequence encoding a heterologous protein of interest operably linked to an isolated harvest inducible regulatory element and a portion of the harvest-inducible gene encoding a harvest-inducible protein or fragment thereof.

The DNA constructs may be ligated or incorporated into an appropriate vector and used to transform plants in order to express heterologous proteins in plants. Accordingly, another aspect of the invention is directed to a plant, plant tissue, plant seed, or plant cell comprising a harvest-inducible regulatory element operably linked with a hetorologous nucleotide sequence and a terminator region.

In yet another aspect of the invention, transgenic plants are produced, the plants comprising a harvest-inducible transgene, the transgene comprising a harvest-inducible regulatory element operably linked to a heterologous nucleotide sequence and a terminator region. The transgene may encode a protein of veterinary or pharmaceutical or biological activity, where the activity is useful for administration to livestock by feeding of whole or parts of harvested plant.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 8 shows the H7 genomic sequence (SEQ ID NO:7), including the 5' flanking regulatory, and coding, regions. The regulatory region is from nucleotide 1 to nucleotide 634 (SEQ ID NO:4) which is the transcription initiation site (bold, large A). Putative TATA boxes are enclosed in a boxed outline. The coding region of the H7 gene is in bold italics and begins at nucleotide 675 and ends at nucleotide 1148 (SEQ ID NO:1); the single letter amino acid sequence of the protein is under the DNA sequence. The 3' UTR starts at 1149 up to the poly A sequence.

FIG. 9 shows the H11 genomic sequence (SEQ ID NO:8) and associated regions. Regulatory region (SEQ ID NO:5, nucleotides 1 to about 438), intron (nucleotides 651-772) and 3' UTR (nucleotides 1239 to the polyA sequence) are in lower case; coding region (nucleotides 439-650 and 773-1238; SEQ ID NO:2) is in upper case and bold.

FIG. 10 shows the H12 genomic sequence (SEQ ID NO:9) and associated regions. Regulatory region (nucleotides 1-936; SEQ ID NO:6), 3' UTR (nucleotides 1720-1906); coding region (nucleotides 976-1720; SEQ ID NO:3) is in upper case and bold.

FIG. 11A shows a vector comprising GUS under the control of an H7 promoter. and NPTII under the control of a NOS promoter. FIG. 11B shows a vector comprising GUS under the control of an H7 promoter, and BAR, under the control of a 35S promoter. FIG. 11C shows a vector comprising GUS under the control of an H11 promoter, and NPTII under the control of a 35S promoter. FIG. 11D shows a vector comprising GUS under the control of an H12 promoter, and NPTII under the control of a 35S promoter. Pro: promoter; T: terminator; RB/LB: right/left borders from T-DNA region of Ti plasmid of Agrobacterium; 35S: from the regulatory region of the 35S transcript of the cauliflower mosaic virus; $\S$: catalase intron in GUS gene.

DESCRIPTION OF PREFERRED EMBODIMENT

Figure 1:
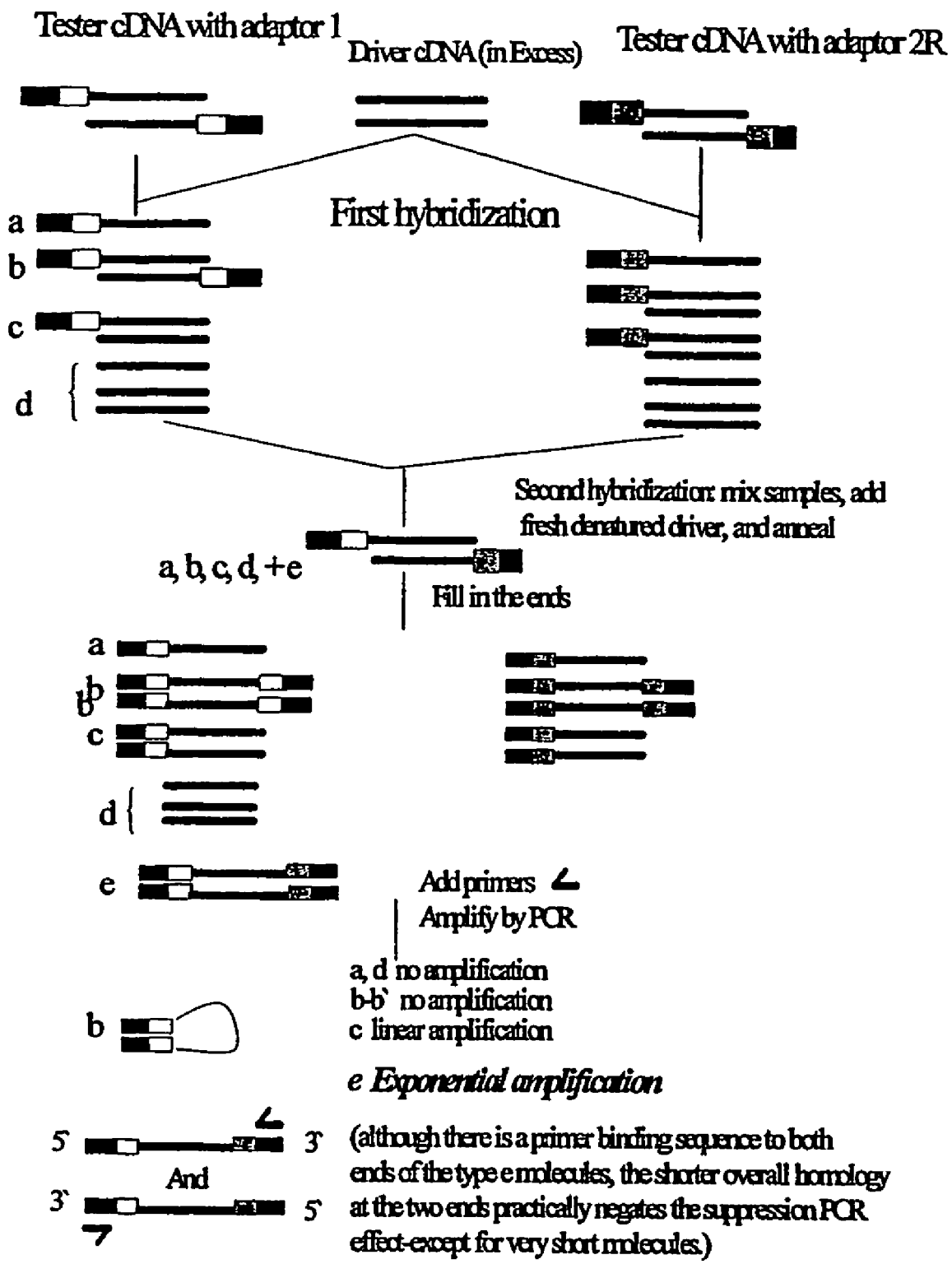
FIG. 1 shows a schematic diagram of PCR-Select cDNA substraction library method for isolating harvest-inducible cDNA clones (see Example 1 for more detail of the method). cDNA containing harvest-specific transcripts is referred to as the "tester" cDNA and the cDNA from the non-harvested plants, referred to as "driver." cDNA Type "e" molecules are formed only if the sequence is up-regulated in the tester cDNA. Solid lines represent the Rsa I digested tester or driver cDNA. Solid boxes represent the outer part of the Adaptor 1 and 2R longer strands and corresponding PCR primer 1 sequence. Clear boxes represent the inner part of Adaptor 1 and the corresponding nested PCR primer 1 sequence; shaded boxes represent the inner part of Adaptor 2R and the corresponding nested PCR primer 2R sequence

The present invention relates to recombinant protein production in plants. More particularly, the present invention relates to novel inducible genes that are expressed upon harvest, and methods to use these genes.

The following description is of a preferred embodiment by way of example only and without limitation to the combination of features necessary for carrying the invention into effect.

The singular forms "a," "an" and "the" include plural reference unless the context clearly dictates otherwise.

Two DNA sequences are "operably linked" if the nature of the linkage does not interfere with the ability of the sequences to effect their normal functions relative to each other. For instance, a promoter, or a regulatory region would be operably linked to a coding sequence if the promoter or regulatory region were capable of effecting transcription of that coding sequence.

By "regulatory region" or "regulatory element" it is meant a nucleic acid sequence that has the property of controlling the expression of a DNA sequence that is operably linked with the regulatory region. Such regulatory regions may include promoter or enhancer regions, and other regulatory elements recognized by one of skill in the art. By "promoter" it is meant the nucleotide sequences at the 5' end of a coding region, or fragment thereof that contain all the signals essential for the initiation of transcription and for the regulation of the rate of transcription.

The term "gene" is used in accordance with its usual definition in the art to mean an operatively linked group of nucleic acid sequences. By operatively linked it is meant that the particular sequences interact either directly or indirectly to carry out their intended function, such as mediation or modulation of gene expression. The interaction of operatively linked sequences may for example be mediated by proteins that in turn interact with the sequences. A transcriptional regulatory region and a sequence of interest are operably linked when the sequences are functionally connected so as to permit transcription of the sequence of interest to be mediated or modulated by the transcriptional regulatory region.

By "coding sequence of interest" it is meant any coding sequence that is to be expressed in a transformed plant. Such a coding sequence of interest may include, but is not limited to, a coding sequence that encodes an antigen, such as a viral coat protein or microbial cell wall or toxin proteins or various other antigenic peptides, such as swine viral antigen. Other proteins or peptides of interest include growth factors, such as epidermal growth factor, antimicrobial peptides, such as defensins, and other peptides with physiological and immunological properties, such as opioids and cytokines, or other pharmaceutically active proteins. Such proteins include, but are not limited to, interleukins, insulin, G-CSF, GM-CSF, hPG-CSF, M-CSF or combinations thereof, interferons, for example, interferon-□α, interferon-β, interferon-τ, blood clotting factors, for example, Factor VIII, Factor IX, or tPA or combinations thereof. Furthermore, a coding sequence of interest may also encode an industrial enzyme, protein supplement, nutraceutical, or a value-added product for feed, food, or both feed and food use. Examples of such proteins include, but are not limited to proteases, oxidases, phytases, chitinases, invertases, lipases, cellulases, xylanases, enzymes involved in oil biosynthesis etc. Other protein supplements, nutraceuticals, or a value-added products include native or modified seed storage proteins and the like. The invention is not limited by the source or the use of the recombinant polypeptide or heterologous nucleotide sequence encoding the polypeptide.

A "transgenic" organism, such as a transgenic plant, is an organism into which foreign DNA has been introduced. A "transgenic plant" encompasses all descendants, hybrids, and crosses thereof, whether reproduced sexually or asexually, and which continue to harbour the foreign DNA.

A "vector" may be any of a number of nucleic acid sequences into which a desired sequence may be inserted by restriction and ligation. A vector typically carries its own origin of replication, one or more unique recognition sites for restriction endonucleases which can be used for the insertion of foreign DNA, and usually selectable markers such as genes coding for antibiotic resistance or herbicide resistance, and often recognition sequences (e.g. promoter) for the expression of the inserted DNA. Common vectors include, but are not limited to, viral vectors, plasmids, phage, phagmids, and cosmids. Vectors may also be modified to contain a region of homology to an *Agrobacterium tumefaciens* vector, preferably a T-DNA border region from *Agrobacterium tumefaciens*. Further, vectors can comprise a disarmed plant tumor inducing plasmid of *Agrobacterium tumefaciens*.

Unless defined otherwise all technical and scientific terms used herein have the same meaning as commonly understood to one of ordinary skill in the art to which this invention belongs.

A nucleotide sequence is said to exhibit "harvest-inducible regulatory activity" when the nucleotide sequence (the first nucleotide sequence, or harvest inducible regulatory element) regulates expression of a second nucleotide sequence to which it is operably linked, following harvesting of plant tissue. A regulatory region (the first nucleotide sequence) that exhibits harvest-inducible regulatory activity (a harvest-inducible regulatory element) may also exhibit activity under other conditions for example but not limited to, wounding, heat shock, or other environmental stresses. Harvest-inducible regulatory activity may result in an increase in the expression of the second nucleotide sequence, or a decrease in the expression of the second nucleotide sequence, when compared to the expression of the second nucleotide sequence under non-harvest conditions. A harvest-inducible regulatory element may therefore be active in increasing or decreasing expression of a second nucleotide sequence to which it is operably linked, relative to the expression of the second nucleotide sequence under non-harvest conditions.

The present invention provides regulatory elements obtained from genes that exhibit modified expression upon harvest of plant tissue. Furthermore, the present invention pertains to the use of these regulatory regions for the expression of heterologous proteins in plants. The present invention is also directed to chimeric constructs containing a DNA of interest operatively linked to a harvest-inducible regulatory element of the present invention. Any exogenous gene, or gene of interest comprising a coding sequence of interest, can be used and manipulated according to the present invention to result in the expression of the exogenous gene.

Harvesting, as is typically carried out in the field involves cutting of plants at the base of the stem at a desired stage of growth, for example but not limited to the late bud stage, and laying cut material in a swath followed by drying at ambient field moisture and temperature conditions to a specific moisture level appropriate for baling or ensiling.

The present invention provides a method to isolate harvest-inducible genes comprising:
 i) constructing a cDNA subtraction library using any suitable method known in the art, from harvested and non-harvested tissues and identifying clones unique to the harvested tissues; and
 ii) identifying sequences preferentially expressed in response to harvesting.

These harvest-inducible cDNA sequences may be characterized using Northern analysis and sequencing.

Examples of harvest-induced cDNA sequences that are preferentially expressed in response to harvesting conditions, and generally not expressed under other conditions typical of cultivation, include, but are not limited to H7, H11 and H12 (SEQ ID NO's: 1-3, respectively), fragments thereof, sequences that hybridize to SEQ ID NO's: 1-3, fragments thereof under stringent hybridization conditions as known in the art, and complements of these sequences, or sequences that exhibit a 80%-100% similarity using sequence alignment protocols, for example, but not limited to, BLAST. The coding region of H7 (SEQ ID NO:1) comprises nucleotides 675-1148 of FIG. 8. The coding region of H11 (SEQ ID NO:2) comprises nucleotide about 439-650 and nucleotides 773-1238 of FIG. 9. The coding region of H12 (SEQ ID NO:3) comprises nucleotides about 976-1720 of FIG. 10.

Stringent hybridization conditions are known within the art (e.g. Sambrook et al, 1989, in "Molecular cloning: a laboratory manual", 2$^{nd}$ edition, Cold Spring Harbor, N.Y.: Cold Spring Harbor Laboratory, which is incorporated herein by reference), and may comprise, hybridization overnight (12-24 hrs) at 42° C. in the presence of 50% formamide, followed by washing using standard protocols (Sambrook et al, 1989), or 5×SSC at about 65° C. for about 12 to about 24 hours, followed by washing in 0.1×SSC at 65° C. for about one hour.

Sequence comparisons between two or more polynucleotides (or polypeptides, as required) may be performed by comparing portions of the two sequences over a comparison window to identify and compare local regions of sequence similarity. The percentage similarity is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity. Optimal alignment of sequences for comparison may be conducted by utilizing readily available sequence comparison and multiple sequence alignment algorithms are, respectively, the Basic Local Alignment Search Tool (BLAST) (Altschul, S. F. et al. 1990. J. Mol. Biol. 215:403; Altschul, S. F. et al. 1997. Nucleic Acids Res. 25: 3389-3402) and ClustalW programs. BLAST is available on the Internet at http://www.ncbi.nlm.nih.gov and a version of ClustalW is available at http://www2.ebi.ac.uk using default parameters (for example but not limited to, Program: blastn; Database:nr; low complexity; Expect 10; Word size 11).

Figure 4:
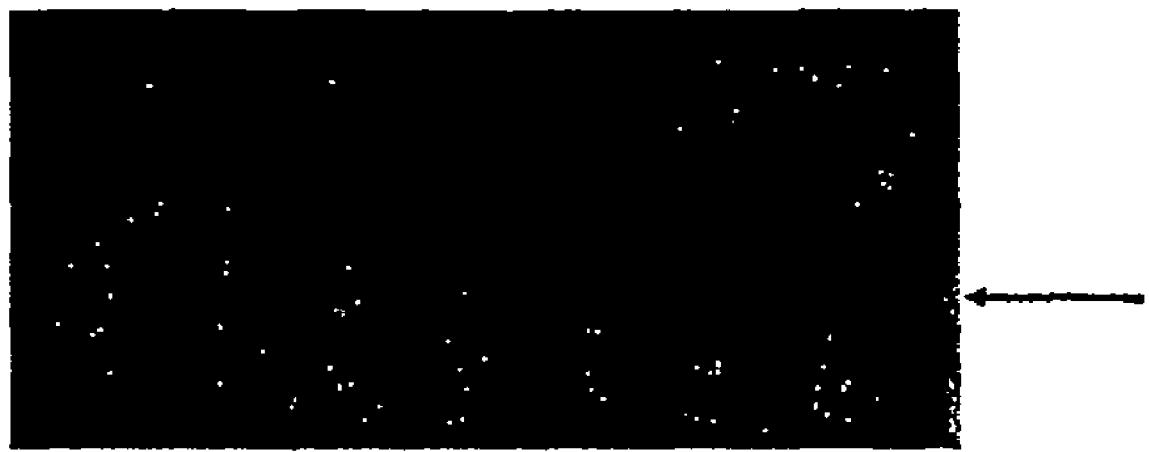
FIG. 4 shows Northern blot analysis of cDNA H11(SEQ ID NO:2) under harvesting and heat shock conditions of treatment of alfalfa leaves. RNA extracted from leaves of: lane 1, non-treated plants; lanes 2-5, plants in harvested conditions for 30 min, 2 hours, 6 hours, 24 hours; lanes 6 and 7, plants subjected to 15 or 30 min of heat shock at 38° C. RNA was probed with H11 cDNA clone (SEQ ID NO:2). Arrow indicates major transcript of H11.
Figure 5:
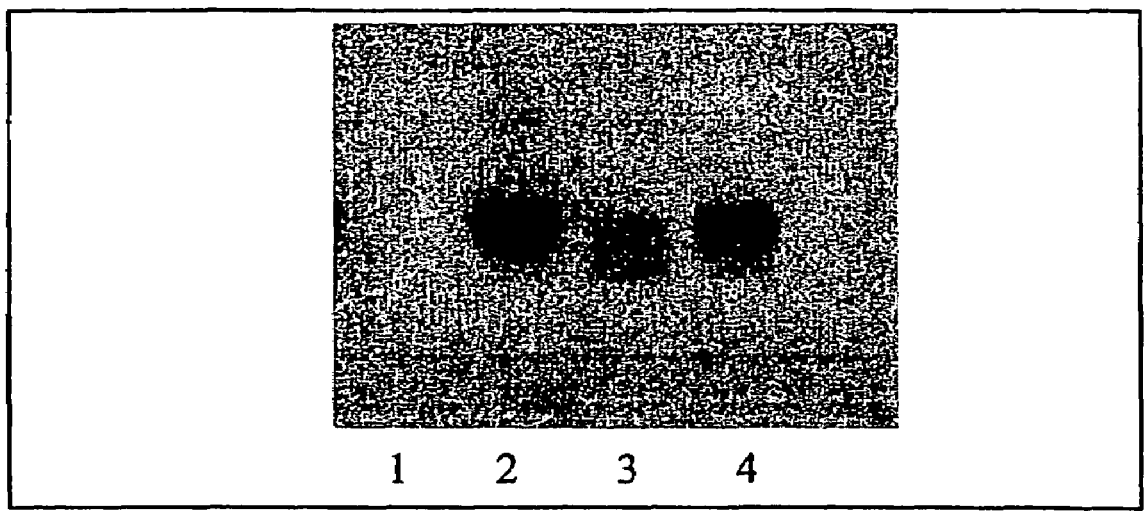
FIG. 5 shows Northern blot analysis of cDNA H11 (SEQ ID NO:2) following wounding of alfalfa leaves. RNA extracted from: lane 1, non-wounded plants; lanes 2-4, plants were wounded using a scalpel and RNA extracted after 45 min, 6, hours, and 24 hours post wounding. RNA was probed with H11 cDNA clone (SEQ ID NO:2)

Using the above method, harvest-inducible cDNA's may be identified and characterized. For example, which is not to be considered limiting in any manner, expression of H7 or H12 is not detected in pre-harvested plant material yet expression increases significantly after tissue is harvested (see FIGS. 3 and 6, respectively). Similarly, H11 expression increases significantly after harvesting (see FIG. 4). However, increase in expression of H11 is also observed in response to heat shock and wounding (FIGS. 4, 5).

Genome walking may be used to identify regulatory regions associated with a harvest-inducible cDNA (see Example 3). Alternatively, harvest-induced cDNA sequences may be used to isolate regulatory elements associated with one or more genomic sequences that are similar to harvest induced cDNA sequences, or that hybridize to harvest induced cDNA sequences under specified hybridization conditions. Regulatory elements thus obtained are capable of conferring harvest-inducibility upon one or more coding sequences of interest that are operably linked to the regulatory elements.

Therefore, the present invention, also relates to the isolation of regulatory elements comprising,
i) isolating genomic DNA from a plant; and
ii) identifying a regulatory region within the genomic DNA using harvest-induced cDNA.

The identified regulatory region may then be further characterized by sequencing and expression analysis, for example, the regulatory region may be used to drive expression of a marker sequence and the activity of the regulatory region analyzed in various tissues and under different environmental or harvest conditions. The regulatory region may be identified using genomic walking using PCR primers identified from harvest-inducible cDNA's. However, other methods that are known in the art may also be used.

Figure 7:
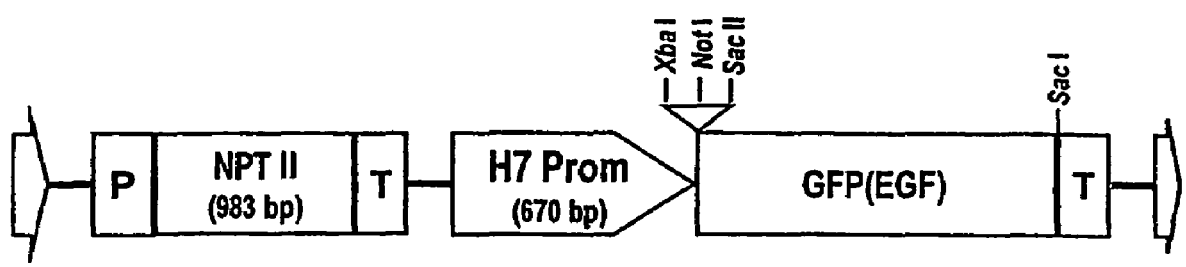
FIG. 7 shows a diagram of a vector construct containing the putative promoter region of an H1 gene and a GFP reporter gene. The arrows represent the left and right borders of the T-DNA region of a binary vector used in Agrobacterium-mediated gene transfer. P represents a promoter used to drive a selective marker such as the resistance gene to the antibiotic neomycin, and T represents a terminator regulatory element such as that derived from nopaline synthase, the CaMV 35S gene or from a plant gene such as H7. The GFP(EGF) coding region following the H7 promoter could represent the coding region of the fluorescent protein, a fusion protein consisting of GFP and EGF (epidermal growth factor), or simply the coding region of EGF alone or any other sequence encoding a peptide or protein with medical or veterinary properties.

A regulatory element identified using the above method may be operably linked with a coding sequence of interest, for example a marker gene, see for example, but not limited to the construct of FIG. 7, and tested to demonstrate harvest inducibility using any suitable technique, for example but not limited to biolistics, protoplast, or *Agrobacterium* transformation, as disclosed herein.

Using the above methods, one or more regulatory regions may be identified that are capable of conferring harvest-inducibility upon a coding sequence of interst operably linked to the regulatory region. Examples, which are not to be considered limiting in any manner, of regulatory elements obtained using the methods of the present invention include SEQ ID NO's: 4-6 (regulatory regions of H7, nucleotides 1-634 of FIG. 8; H11, nucleotides 1 to about 438 of FIG. 9; and H12, nucleotides 1-935 of FIG. 10, respectively), fragments thereof, or sequences that hybridize to SEQ ID NO's: 4-6, or their complement, under stringent hybridization conditions (e.g. hybridization overnight (12-24 hrs) at 42° C. in the presence of 50% formamide, followed by washing using standard conditions, or 5×SSC at about 65° C. for about 12 to about 24 hours, followed by washing in 0.1×SSC at 65° C. for about one hour) or that exhibit a 80%-100% similarity using sequence alignment protocols, for example, but not limited to, BLAST (Program: blastn; Database:nr; low complexity; Expect 10; Word size 11), provided the sequence exhibits harvest-inducible regulatory element activity.

The present invention therefore provides DNA constructs useful for producing a protein or peptide of interest within a plant. Examples of DNA constructs of the present invention, which are not to be considered limiting in any manner, include a coding sequence of interest operably linked to a harvest inducible regulatory element, or a nucleotide sequence encoding the protein of interest fused to a nucleotide sequence encoding a harvest-induced protein, or a portion thereof, where the nucleotide sequence encoding the harvest-induced protein or portion thereof is operably linked to a harvest-inducible regulatory element. This latter construct may be used to ensure stability of a protein of interest following expression in a plant. It is also contemplated that peptide sequences that facilitate isolation, purification, or both of the protein of interest, for example affinity tags, protease cleavage sites, or both may be included in the DNA constructs. These DNA constructs may be introduced into an expression cassette suitable for plant transformation.

The present invention is also directed to a method for production of a protein or peptide of interest comprising,
i) introducing a construct comprising a coding sequence of interest operably linked to a harvest inducible regulatory element into a plant, to obtain a transgenic plant;
ii) growing the transgenic plant; and
iii) harvesting the transgenic plant thereby inducing production of the protein of interest.

If required, the protein or peptide of interest may be recovered after harvest.

Additionally, the present invention provides a method for production of a protein or peptide of interest comprising,
i) providing a plant comprising a construct comprising a coding sequence of interest operably linked to a harvest inducible regulatory element;
ii) growing the plant; and
iii) harvesting the plant thereby inducing production of the protein or peptide of interest.

If required, the protein or peptide of interest may be recovered after harvest.

The HI promoters of the present invention are similarly regulated across plant families and genera, such that they have applications in crops of various species. Thus, this method may be used with any desired plant, for example but not limited to potato, tomato, canola, corn, soybean, alfalfa, pea, lentil, other forage legumes such as clover, trefoil, forage grasses such as timothy, ryegrass, brome grass, fescue or other cereal grasses used for forage such as barley, wheat, sudan grass, sorgham.

The present invention also provides a method for enhancing translation, stability, recovery, or a combination thereof, of a protein or peptide of interest upon harvest of a plant tissue comprising:
i) introducing a construct comprising a coding sequence of interest fused to a nucleotide sequence encoding a harvest-induced protein, or a portion thereof into a plant to obtain a transgenic plant, where the nucleotide sequence encoding the harvest-induced protein or portion thereof is operably linked to a harvest-inducible regulatory element;
ii) growing the transgenic plant; and
iii) harvesting of the transgenic plant to induce expression of the protein or peptide of interest.

If required, the protein or peptide of interest may be recovered after harvest.

Furthermore, a method for enhancing translation, stability, recovery, or a combination thereof, of a protein or peptide of interest upon harvest of a plant tissue is also provided, the method comprising:
i) providing a plant comprising a construct, the construct comprising a coding sequence of interest fused to a nucleotide sequence encoding a harvest-induced protein, or a portion thereof, where the nucleotide sequence encoding the harvest-induced protein or portion thereof is operably linked to a harvest-inducible regulatory element;
ii) growing the plant; and
iii) harvesting the plant to induce expression of the protein or peptide of interest.

If required, the protein or peptide of interest may be recovered after harvest.

As the HI promoters of the present invention are similarly regulated across plant families and genera, this method may be used with any desired plant, for example but not limited to potato, tomato, canola, corn, soybean, alfalfa, pea, lentil, other forage legumes such as clover, trefoil, forage grasses such as timothy, ryegrass, brome grass, fescue or other cereal grasses used for forage such as barley, wheat, sudan grass, sorgham.

With either of the above methods, the protein of interest may be isolated and purified, as required, using standard techniques known in the art.

The methods provided herein may be used to produce heterologous proteins of interest in a plant, and allows for the production of crop plants specifically designed for molecular farming wherein plants produce novel proteins with commercial or pharmaceutical applications.

Of particular interest are those proteins or peptides that may have a therapeutic value, for example vaccines. Vaccines produced by the methods of the present invention include antigens, such as viral coat proteins or microbial cell wall or toxin proteins or various other antigenic peptides, such as swine viral antigen. Other proteins or peptides of interest include growth factors, such as epidermal growth factor, antimicrobial peptides, such as defensins, and other peptides with physiological and immunological properties, such as opioids and cytokines. The invention is not limited by the source or the use of the recombinant polypeptide or heterologous nucleotide sequence encoding the polypeptide.

Examples of other proteins which may be produced in plants or crops by using the regulatory elements, constructs, or methods of the present invention, and that may be considered as genes of interest, include but are not limited to, industrial enzymes, for example, proteases, carbohydrate modifying enzymes such as alpha amylase, glucose oxidase, cellulases, hemicellulases, xylanases, mannases or pectinases, (for example U.S. Pat. Nos. 5,824,870, 5,767,379, 5,804,694). Additionally, the production of enzymes particularly valuable in the pulp and paper industry such as ligninases or xylanases is also contemplated (for example U.S. Pat. No. 5,981,835). Other examples of enzymes include phosphatases, oxidoreductases and phytases (for example U.S. Pat. No. 5,714,474). The number of industrially valuable enzymes is large and plants can offer a convenient vehicle for the mass production of these proteins at costs anticipated to be competitive with fermentation, provided the production system is efficient and easily manipulated. Also contemplated are protein-based elastomers to replace allergenic compounds such as latex.

Additionally, molecular farming is also being contemplated for use in the production and delivery of vaccines (for example, U.S. Pat. Nos. 6,136,320, 5,914,123, 5,679,880, 5,679,880, 5,654,184, 5,612,487, 6,034,298, WO 99/37784A1), antibodies (for example, WO 97/2900A1, U.S. Pat. Nos. 5,959,177, 5,202,422, 5,639,947, 6,046,037), peptide hormones (for example, U.S. Pat. No. 5,487,991, WO 99/6740A2), blood factors and similar therapeutic molecules. It has been postulated that edible plants which have been engineered to produce selected therapeutic agents could provide a means for drug delivery which is cost effective and particularly suited for the administration of therapeutic agents in rural or under developed countries. The plant material containing the therapeutic agents could be cultivated and incorporated into the diet (for example U.S. Pat. No. 5,484,719). Similarly, plants used for animal feed can be engineered to express veterinary biologics that can provide protection against animal disease, (for example WO 99/37784A1).

The DNA sequence encoding the protein of interest may be synthetic, naturally derived, or a combination thereof. Dependent upon the nature or source of the DNA encoding the polypeptide of interest, it may be desirable to synthesize the DNA sequence with codons that represent plant-preferred codons. It is contemplated that the coding region of the protein of interest can be joined to the coding sequence of a harvest-inducible protein obtained as described herein, to aid in stability or accumulation, or to provide a convenient means to isolate the protein.

The chimeric DNA constructs of the present invention can further comprise a termination (or 3' untranslated) region. A termination region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5-AATAAA-3 although variations are not uncommon.

Examples of suitable termination regions are the 3' transcribed non-translated regions containing a polyadenylation signal of *Agrobacterium* tumour inducing (Ti) plasmid genes, such as the nopaline synthase (Nos gene) and plant genes such as the soybean storage protein genes and the small subunit of the ribulose-1,5-bisphosphate carboxylase (ssRUBISCO) gene.

The termination region operably linked to the heterologous gene will be primarily one of convenience, since in many cases termination regions appear to be relatively interchangeable.

The DNA constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

The DNA constructs of the present invention can further comprise signal peptides operably linked to a gene of interest such that expression is targeted to a specific organelle.

A variety of techniques are available for the introduction of DNA into host cells. For example, the chimeric DNA constructs may be introduced into host cells using standard *Agrobacterium* vectors by transformation protocols (EP 131320 B1, U.S. Pat. Nos. 5,591,616, 5,149,645, 4,693,976; all of which are incorporated herein by refernece). The use of T-DNA for transformation of plant cells has received extensive study and is amply described in EP 120516 (also see Hoekema et al., 1985, Chapter V, In: The Binary Plant Vector System Offset-drukkerij Kanters B. V., Alblasserdam; Knauf, et al., 1983, Genetic Analysis of Host Range Expression by *Agrobacterium*, p. 245, In: Molecular Genetics of the Bacteria-Plant Interaction, Puhler, A. ed., Springer-Verlag, NY; and An et. al., 1985, EMBO J., 4:277-284, which are incorporated herein by reference).

The use of non-*Agrobacterium* techniques permits the use of the constructs described herein to obtain transformation and expression in a wide variety of monocotyledonous and dicotyledonous plants and other organisms. These techniques include biolistics (U.S. 5,865,796, 5,120,657, 5,371, 015, 5,179,022; which are incorporated herein by reference), electroporation (U.S. 5,859,327, 6,002,070; Fromm et al., 1985, Proc. Natl. Acad. Sci. USA, 82:5824-5828; Riggs and Bates, 1986, Proc. Natl. Acad. Sci. USA 83:5602-5606; which are incorporated herein by reference), microinjection of protoplasts, (U.S. Pat. No. 4,743,548, which is incorporated herein by reference), penetration of cells with tungsten whiskers, (U.S. Pat. No. 5,302,523, 5,464,765, which are incorporated herein by reference), lasers, (U.S. Pat. No. 5,013,660, which is incorporated herein by reference), sonification, (U.S. Pat. No. 5,693,512, which is incorporated herein by reference) or PEG-mediated DNA uptake (Potrykus et al., 1985; Mol. Gen. Genet., 199:169-177; U.S. Pat. No. 5,453,367, which are incorporated herein by reference).

The expression cassette may be joined to a marker for selection in plant cells. Conveniently, the marker may be resistance to a herbicide, eg phosphinthricin oer glyphosate, (U.S. Pat. Nos. 5,4553,367, 4,940,835, 5,648,477) or an antibiotic, such as kanamycin, 6418, bleomycin, hygromycin, chioramphenicol, (for example U.S. Pat. Nos. 5,116, 750, 6,048,730) or the like. Similarly, enzymes providing for production of a compound identifiable by colour change such as GUS (□-glucuronidasebeta), or luminescence, such as luciferase or GEP are also useful.

Also considered part of this invention are transgenic plants containing the gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

Plants thus obtained may be cultivated and used for the production of various proteins. It is envisioned that for some applications the harvested material will be subject to purification and the heterologous protein isolated in a substantially pure form. In other instances the harvested plant material will be used as edible or oral-vaccines or therapeutic agents. In addition, the foreign protein of interest may be purified from the harvested plant material and may be formulated into a form for oral use or an injectable dosage form. In still other examples the harvested plant material may be used directly in an industrial process. Thus, the isolation of harvest inducible DNA sequences allow for many strategies for the production of heterologous proteins.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

Isolation of Harvest-Inducible (HI) cDNA Clones

HI cDNAs were isolated from a cDNA subtractive library, made from mRNA obtained from field harvested alfalfa, as shown in FIG. 1, using a PCR-Select™ kit from ClonTech (Protocol #Pt1117-1, see URL: clontech.com). Briefly, this technique compares two populations of mRNA and obtains clones of genes that are expressed in one population but not in the other.

First, two mRNA populations were converted into cDNA: the cDNA that contained the harvest-specific transcripts, referred to as the "tester" cDNA and the reference cDNA from the non-harvested plants, referred to as "driver" cDNA. The tester and driver cDNAs were digested with Rsa I (a four-base-cutting restriction enzyme that yields blunt ends). The tester cDNA was subdivided into two portions, and each ligated with a different cDNA adaptor. The ends of the adaptor do not have a phosphate group, so only one strand of each adaptor attaches to the 5' ends of the cDNA. The two adaptors have stretches of identical sequence to allow annealing of the PCR primer once the recessed ends have been filled in (See FIG. 2).

Two hybridizations were then performed. In the first, an excess of driver was added to each sample of tester. The samples were then heat denatured and allowed to anneal, generating the type a, b, c, and d molecules in each sample (see FIG. 1). The concentration of high- and low-abundance sequences is thought to be equalized among the type a molecules because reannealing is faster for the more abundant molecules due to the second-order kinetics of hybridization. At the same time, the single stranded (ss) type a molecules are significantly enriched for differentially expressed sequences, as cDNAs that are not differentially expressed form type c molecules with the driver.

Figure 2:
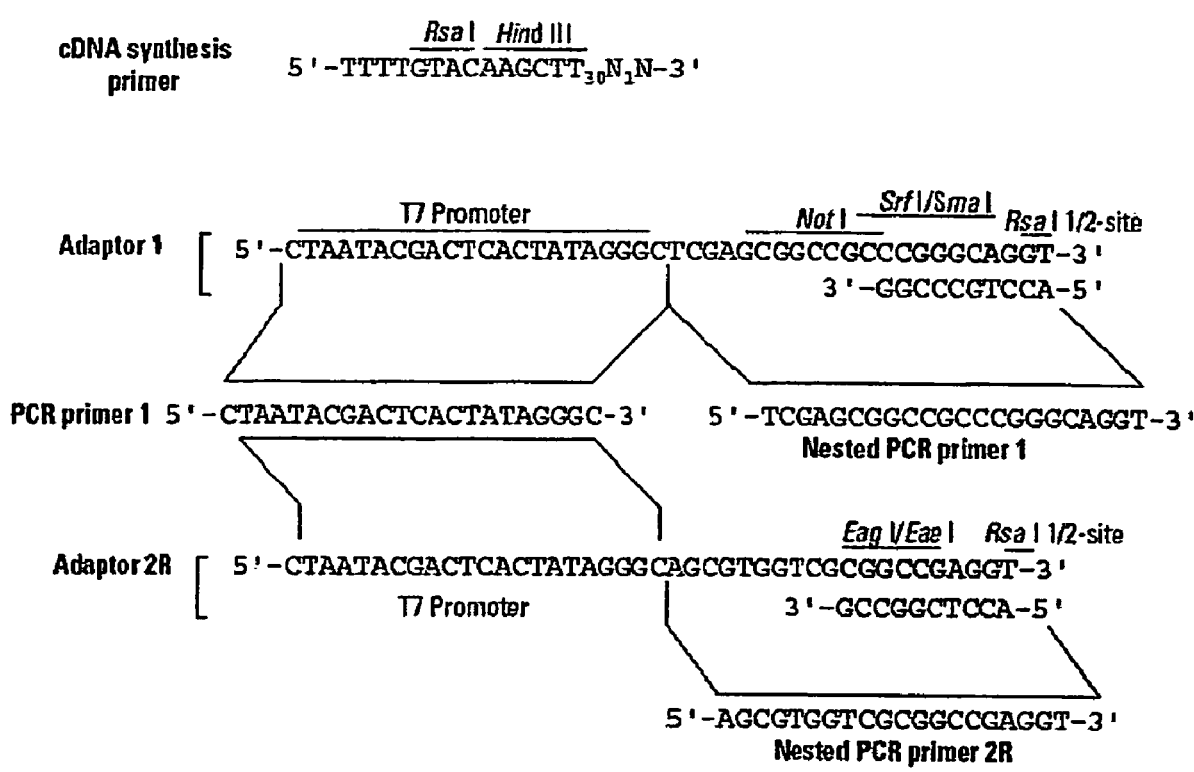
FIG. 2 shows sequences of PCR-Select cDNA synthesis primer (SEQ ID NO:12), adaptors 1 and 2R (SEQ ID Nos: 13-14), PCR primer 1 (SEQ ID NO: 15) and nested PCR primers 1 and 2R (SEQ ID Nos: 16-17). When the adaptors are ligated to Rsa1-digested cDNA, the Rsa1 site is restored.

During the second hybridization, the two primary hybridization samples were mixed together without denaturing. As a result, only the remaining equalized and subtracted ss tester cDNAs could reassociate and form new type e hybrids. These new hybrids are double stranded (ds) tester molecules with different ends, which correspond to the sequences of adaptors 1 and 2R (FIG. 2). Fresh denatured driver cDNA was added, without denaturing the subtraction mix, to further enrich fraction e for differentially expressed sequences. After filling in the ends by DNA polymerase, the type e molecules—the differentially expressed (harvest-inducible) tester sequences—have different annealing sites for the nested primers on their 5' and 3' ends.

The entire population of molecules was then subjected to PCR to amplify the harvest-inducible sequences. During PCR, type a and d molecules are missing primer annealing sites, and thus cannot be amplified. Due to the suppression PCR effect, most type b molecules form a pan-like structure that prevents their exponential amplification (see Suppression-PCR effect, below). Type e molecules have only one primer annealing site and can only be amplified linearly. Only type e molecules, which have two different adaptors, can be amplified exponentially. These are the equalized, differentially expressed sequences specific to harvested tissue.

Next, a secondary PCR amplification was performed using nested primers to further reduce any background PCR products and to enrich for harvest-specifc sequences. The cDNAs were then directly inserted into Topo™, a T/A cloning vector from Invitrogen.

Suppression-PCR

The PCR-Select cDNA adaptors are engineered to prevent undesirable amplification during PCR using suppression PCR (U.S. Pat. No. 5,565,340). Suppression occurs when complementary sequences are present on each end of a ss cDNA. During each primer annealing step, the hybridization kinetics strongly favor (over annealing of the shorter primers) the formation of a pan-like secondary structure that prevents primer annealing. When occasionally a primer anneals and is extended, the newly synthesized strand will also have the inverted terminal repeats and form another pan-like structure. Thus, during PCR, nonspecific amplification is efficiently suppressed, and specific amplification of cDNA molecules with different adaptors at both ends can proceed normally. The 5' ends of Adaptors 1 and 2R have an identical stretch of 22 nucleotides (FIG. 2). Primary PCR therefore requires only one primer for amplification, eliminating the problem of primer dimerization. Furthermore, the identical sequences on the 3' and 5' ends of the differentially expressed molecules introduce a slight suppression PCR effect. Since these identical sequences are the same length as PCR Primer 1, the suppression effect becomes significant only for very short cDNAs (under 200 nt), because the formation of pan structures for shorter molecules is more efficient. Thus, longer molecules are preferentially enriched. This enrichment for longer molecules balances the inherent tendency of the subtraction procedure to favor short cDNA fragments, which are more efficiently hybridized, amplified, and cloned than longer fragments.

Plant Material

The field of alfalfa (c.v. Gala, Northrup King), located on the south edge of Guelph, was in its second year after planting, and had already undergone its first harvest of the season. Plants at the bud stage and ready for the second harvest were cut approximately 8 cm from the base from a 1.0 $m^2$ area The temperature in the field was approximately 25-28° C., and the harvesting was performed at noontime to avoid humidity. The control, non-harvest-treatment plant tissue was immediately frozen in liquid nitrogen. The harvest-treatment sample was laid on the ground in a swath to wilt, as is done during conventional harvesting of this crop. After one hour, the harvested plant tissue was brought back to the lab, wrapped in tinfoil and left at ambient temperature (20° C.) on the bench.

The leaves were collected for the analysis at different harvest times—30 minutes, 45 minutes, 2 hours, 6 hours, 24 hours. Total RNA was isolated from both non-harvested and harvested plant materials. cDNA was generated from both tissues with HI samples designated as the tester population and the non-harvested samples were designated as the driver population. Harvest-inducible cDNAs were inserted into TOP02.1 vector (Invitrogen).

Twelve cDNA clones, ranging in size from 180 to 500 bp, were obtained using the subtractive protocol outlined above. These clones were sequenced to determine redundancy and to select candidates for further analysis. Seven clones of the 12 were independent and 4 (H1, H7, H11, and H12) were selected for Northern analysis. Of these, H7 (SEQ ID NO:1), H11 (SEQ ID NO:2) and H12 (SEQ ID NO:3) showed substantial and lengthy (>24 h) up-regulation following harvest and no transcription in non-harvested plants (see Northern blots, Example 2)

The DNA sequence of selected clones was determined and GeneBank searches performed using BLAST searching algorithm (default parameters).

Isolation of Complete cDNA Clones

To isolate the regulatory regions of H7 and H11 the complete coding region of these genes was identified. This was done by extending our candidate cDNA clones in both the 5' and 3' directions using the RACE (rapid amplification of cDNA ends) method.

Specifically, a cDNA population was generated from alfalfa leaves (c.v. Gala) grown in a greenhouse 12 hours after harvesting using the SMART™ RACE cDNA Amplification Kit from ClonTech according to manufacturer's instructions. Harvested plants were wilted for one hour in the greenhouse followed by wrapping in tin foil and incubation on the lab bench at 20° C. By this method of repeated "cDNA walking" and isolation of many cDNA clones overlapping each other and the original cDNA clone isolated by subtraction, the full-length transcripts were accurately determined for H7 (SEQ ID NO:1) and H11 (SEQ ID NO:2). The regulatory regions flanking the coding region were then isolated by genomic walking (see below).

As H12 (SEQ ID NO:3) was virtually identical to an alfalfa cDNA already characterized and resident in GenBank, we did not extend H12 by RACE, but rather performed genomic walking upstream of the 5' end of the cDNA based on the sequence data available. The sequence of H12 shows homology to a cDNA from alfalfa that presumably encodes the enzyme CcoMT, thought to be involved in lignin formation (see FIG. 7 for sequence comparison).

Example 2

Analysis of Expression Patterns of Harvest Inducible (II) cDNAs

Northern blots were done using standard protocols (Sambrook et al, 1989, in "Molecular cloning: a laboratory manual", 2nd edition, Cold Spring Harbor, N.Y. Cold Spring Harbor Laboratory). Equivalent amounts of total RNA from harvest-induced, heat-shock treated and wounded leaf tissue were used for hybridization. The hybridizations were overnight (12-24 hrs) at 42° C. with $^{32}$P-labelled HI cDNA presence of 50% formamide, followed by washing using standard protocols (Sambrook et al, 1989). A wounding treatment was applied to alfalfa plants by lightly scoring a leaf with a surgical blade on the leaf surface. The wounded leaves were removed from the plants for analyses 30 minutes, 6 hour and 24 hours post treatment. Heat-shock treatments were performed by placing potted alfalfa plants into an oven for 15 minutes or 30 minutes at 38° C. The tissue samples were collected from the plants immediately following heat treatment. mRNA accumulation for cDNA clones H7, H11 and H12 were examined under harvest conditions. The Northern analysis results showed significant mRNA accumulation following harvesting but not wounding (Table 1, FIGS. 3-6).

TABLE 1

Relative accumulation of HI cDNAs following harvesting, wounding and heat shock treatments compared with untreated tissue.

| cDNA clones | Relative transcript level under different treatments | | |
|---|---|---|---|
| | harvest | heat shock | wounding |
| H1 | +* | ? | ? |
| H7 | ++ | − | − |
| H11 | ++ | +++ | ? |
| H12 | ++ | − | ? |

*"+" and "++" are results compared with control sample where control is consider as "−".

Figure 3:
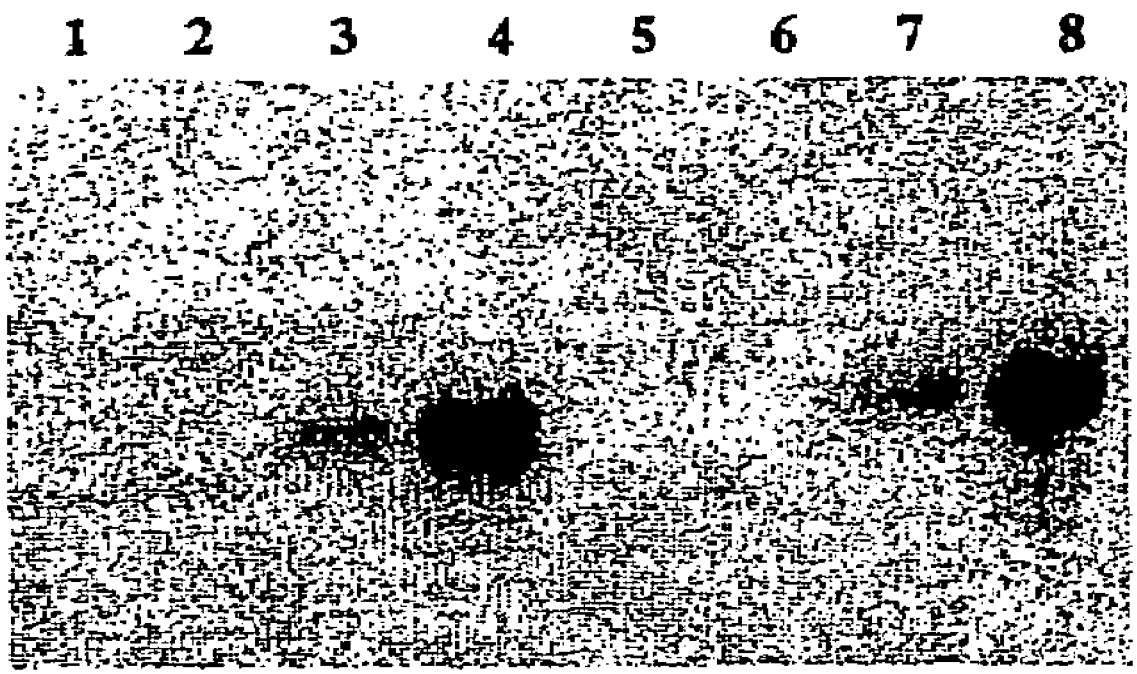
FIG. 3 shows Northern blot analysis of the expression of cDNA H7 following harvest of leaf tissue. RNA was isolated from alfalfa leaves and probed with H7 (SEQ ID NO:1). Leaves obtained before harvest (lanes 1, 5), 45 min post harvest (lanes 2, 6), 6 hours post harvest (lanes 3, 7) and 24 hours post harvest (lanes 4, 8). H7 RNA is not detected in alfalfa leaves in non-harvest, i.e. pre-harvest conditions nor following wounding or heat treatments (data not shown).

Northern analysis of H7 (SEQ ID NO:1) expression before or after harvest is shown in FIG. 3. H7 expression increases following harvest, however, no expression is observed pre-harvest, or following wounding or heat shock treatments (data not shown).

Expression of H11 (SEQ ID NO:2) following harvesting or heat shock is shown in FIG. 4. Increased expression is observed following harvesting or heat shock treatment. Similarly, increased expression of H11 is observed following wounding (FIG. 5).

Figure 6:
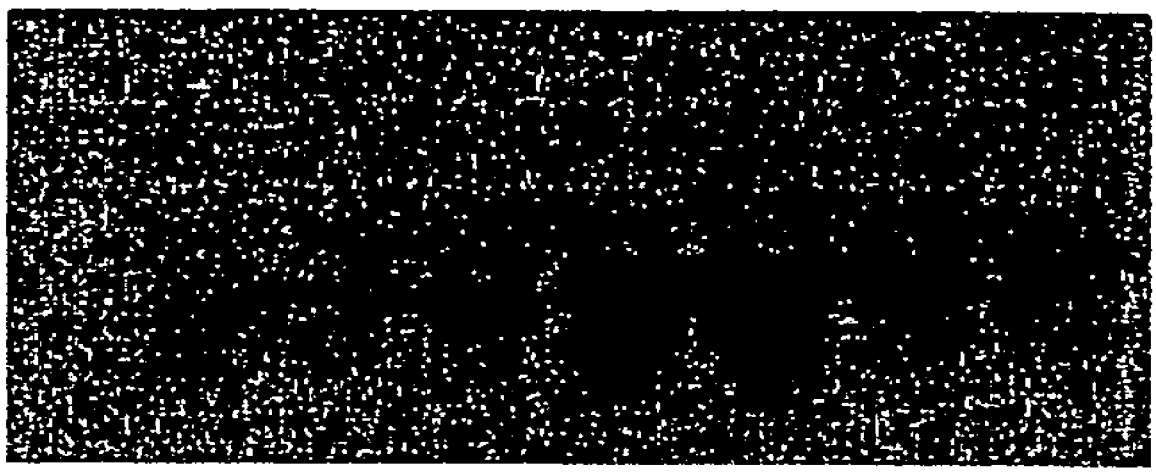
FIG. 6 shows a Northern blot analysis of cDNA clone H12 (SEQ ID NO:3) following harvesting and heat shock treatments of alfalfa leaves. RNA extracted from leaves of: lane 1, non-treated plants; lanes 2-5, plants in harvested conditions for 30 min, 2 hours, 6 hours and 24 hours; lanes 6 and 7, plants subjected to 15 or 30 min of heat shock at 38° C.

H12 (SEQ ID NO:3) expression is shown in FIG. 6, where an increase in expression is observed following harvest of plant material. No expression is observed in pre-harvested tissue. A low level of expression is detected in response to a heat shock treatment.

Example 3

Isolation of Genomic Sequences and Promoter Regions of HI Genes

Alfalfa leaf tissue was collected from plants grown in the greenhouse. Genomic DNA was isolated using a method modified from Davies (Davies L G, Dibner M D, Batty J F: Basic methods in molecular biology. Elsevier, N.Y. 1986, which is incorporated herein by reference). Construction of the genomic walking. "library" was performed according to the manufacturer's manual (GenomeWalker™ Kits CLONTECH, USA PT116-1). DNA from colonies was sequenced to find those containing inserts overlapping the cDNA-labelled cDNA clones H7, H11 and H12 were used for screening of the library.

As a result of this screening, corresponding genomic DNAs, of H7 (SEQ ID NO:7, FIG. 8), H11 (SEQ ID NO:8, FIG. 9), and H12 (SEQ ID NO:9, FIG. 10) were obtained. Further analysis of these genomic DNA's was carried out to identify the associated regulatory regions of H7 (SEQ ID NO:4), H11 (SEQ ID NO:5) and H12 (SEQ ID NO:6).

The regulatory regions of these genes may be used to drive the expression of a coding sequence of interest, for example, but not limited to the coding sequence of interest as shown in FIG. 7.

Example 4

Transgenic Plants Expressing Harvest-Inducible Promoters

Vector Construction

In order to test expression of transgenes controlled by the harvest inducible (HI) promoters isolated from alfalfa, the HI promoters were fused to the beta-glucuronidase (GUS) reporter gene and histochemical assays conducted for GUS gene activity, which results in a blue colour in plant tissue (Jefferson et al., 1987, EMBO J. 6:3901-7). The putative HI promoter sequences were sub-cloned from Topo (InVitrogen) or pBluescript vectors using conventional molecular techniques and existing restriction sites or sites created by polymerase chain reaction (PCR).

Figure 11:
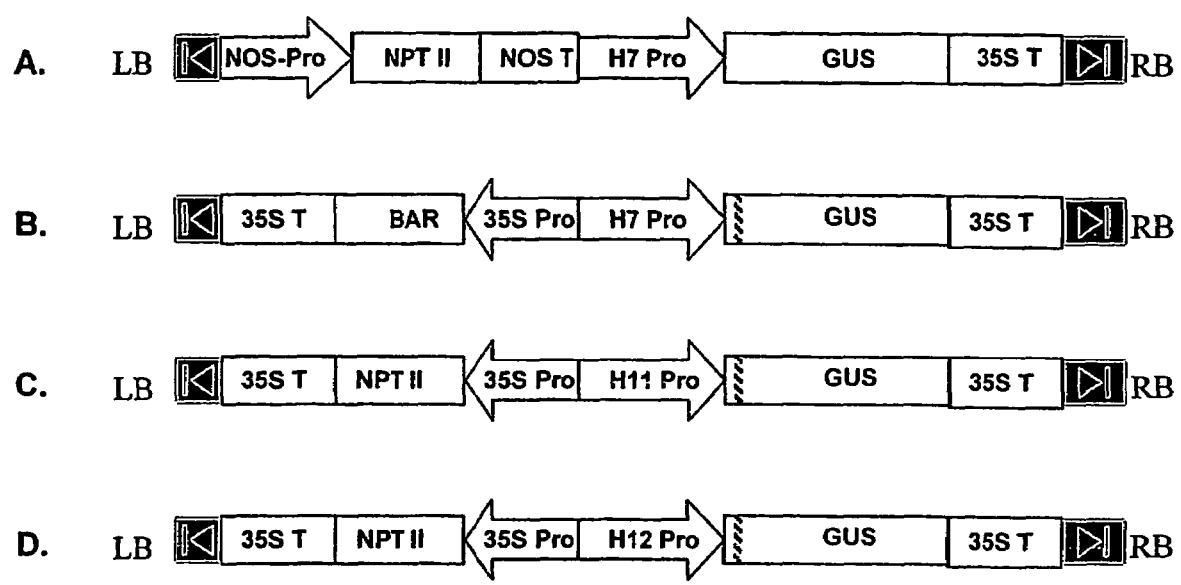
FIG. 11 shows binary vectors containing harvest-inducible promoters fused to the GUS gene.

The putative promoter region for the H7 cDNA clone was fused to the 5' terminus of the GUS gene in the vector pBI101 (Jefferson et al., 1987, EMBO J. 6:3901-7, FIG. 1a), using HindIII and Xba1; in addition, the H7 promoter was fused to the GUS gene in pCAMBIA3301 (CAMBIA), using KpnI and Xba1 (FIG. 11B). The H11 promoter was fused to pCAMBIA2301, and the H12 promoter was fused to pCAMBIA1303 (FIGS. 11C, D). In all cases, the promoter is also 5' to the GUS gene.

All of the above vectors are of the binary type, which means they can be grown in both E. coli and Agrobacterium, the latter for transfer of the regions between the left and right borders to the plant genome.

Transfer of HI-GUS Constructs to Plants

The binary vectors were transferred to Agrobacterium tumefaciens strain C58 (Rif res) containing the helper plasmid pMP90. The procedure for cocultivation of sterile leaves from 4-week old tobacco plants (cultivar PetH4) and regeneration followed the method of Fisher and Guiltinan (Fisher & Guiltinan, 1995, Plant Mol Biol Rep. 13:278-89). Selection of transgenic tissue and shoots was facilitated by incorporation of kanamycin (300 mg/l) or hygromycin (25 mg/l), depending on the vector used (see FIG. 11).

The binary vectors were also used to transfer HI-GUS constructs to Medicago truncatula according to the seedling infiltration method of Trieu et al. (Trieu A T, et al., 2000, Plant J. 22:531-41).

Histochemical GUS Assays for Transgene Expression

Tobacco leaves from regenerated plants grown in the greenhouse, and leaves and stems from M. truncatula plants grown from the cocultivated seedlings were incubated in the X-gluc substrate and the green pigments removed for visualization of the blue precipitate resulting from GUS enzyme activity (Jefferson et al., 1987, EMBO J. 6:3901-7).

Results

Figure 12:
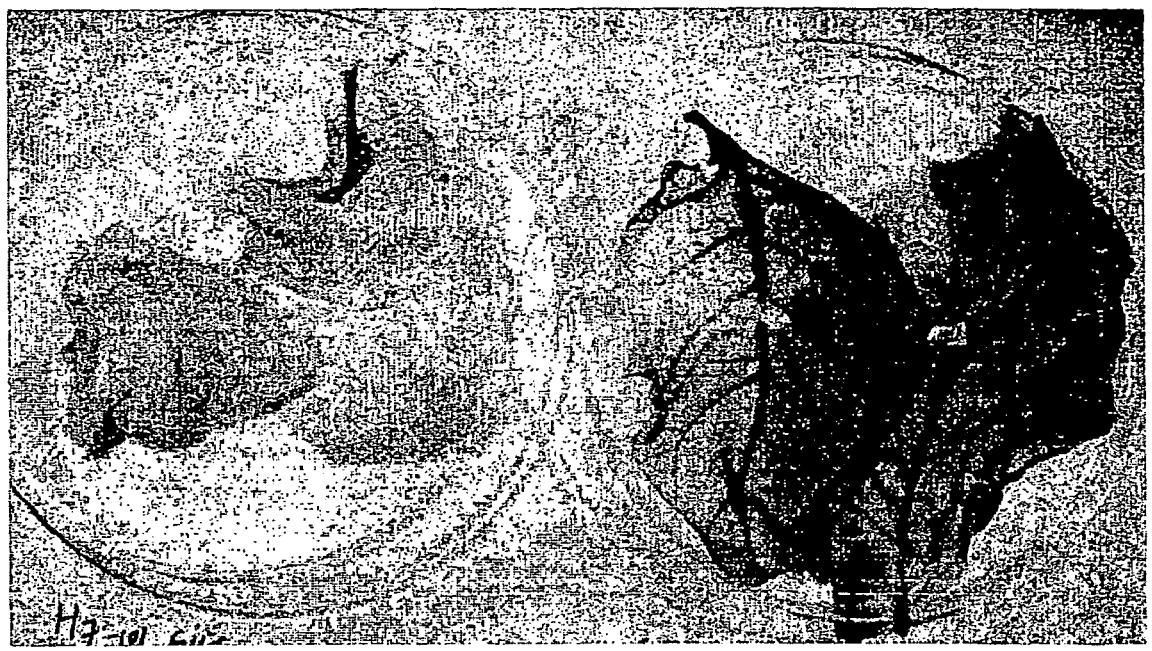
FIG. 12 shows the expression of H7-GUS in tobacco at time zero (left) and 24 hours post-harvest (right).
Figure 13:
FIG. 13 shows GUS expression in random samples from M. truncatula plants grown from seedling co-cultivated with Agrobacterium. Upper left plate: H12-GUS (24 hours post-harvest); upper right plate: H11-GUS (24 hours post-harvest); lower left: H7-GUS (24 hours post-harvest); lower middle: 35S-GUS (24 hours post-harvest); lower right: untransformed control. The chimeric nature of transformation events results in non-blue sectors of plants, and hence leaves and stems showing no blue coloration.

Analysis of tobacco R0 (primary) regenerants, 5-10 plants for each of the above constructs, showed GUS gene expression (i.e. blue colouration) 24 hrs following harvesting whereas none was evident in plants at time zero or in the non-transgenic controls (FIG. 12). Random sampling of portions (leaves and stem/petiole sections) of the M. truncatula plants that had undergone cocultivation at the seedling stage also revealed distinct blue colouration in some sectors, but not in all parts and only after the harvesting treatment (FIG. 13). The sectoral pattern of the blue stain reflects the chimeric nature of gene transfer, and the cocultivation of intact seedlings. Once again, no blue colour was evident in the transgenic plants at time zero or in the non-transgenic controls. It is also significant that the extent of blue colouration was greater in the case of constructs containing the H11 and H7 promoters than in plants containing the conventional 35S promoter. The lack of blue colour in transgenic trunculata plants at time zero demonstrates that the blue colour was not due to endogenous GUS activity in residual *Agrobacteria*.

The extent and intensity of blue colouration in the HI-GUS plants of the present invention noticeably exceeds that of plants containing the GUS gene controlled by the 35S promoter. The latter promoter is derived from the cauliflower mosaic virus and is considered to be a constitutive promoter, which provides a high level of expression to transgenes, especially in tobacco. Therefore, not only do the HI promoters of the present invention avoid the problems associated with constitutive expression, but they also exceed the levels of expression provided by one of the strongest constitutive promoter available for plants.

As presently shown, the expression of the HI promoters is tightly regulated in that repeatedly no expression has been observed in the transgenic plants of the present invention at time zero, and does not appear until several hours after harvesting. It is also significant that no additional wounding of the plant tissue is needed to obtain high expression levels throughout all harvested tissue, although additional wounding or other treatments such as heat may augment expressions levels even further.

Furthermore, the HI-GUS transgenes show the same harvest-specific induction patterns in tobacco and *M truncatula* as do the native cDNA clones in alfalfa from which they were isolated under harvesting conditions. Although *M trunculata* is a close relative of alfalfa, tobacco is quite distant phylogenetically from alfalfa. This shows that the HI promoters of the present invention are regulated in a similar pattern in other plant families and genera, such as the grass species and have applications in crops of such species.

The following table (Table 2) is a summary of the Sequence ID numbers defined in the present application.

TABLE 2

Sequence ID numbers defined in the present invention.

| Sequence ID No. | Description | Figure |
| --- | --- | --- |
| SEQ ID NO: 1 | Nucleotide sequence of H7 coding region | 8 |
| SEQ ID NO: 2 | Nucleotide sequence of H11 coding region | 9 |
| SEQ ID NO: 3 | Nucleotide sequence of H12 coding region | 10 |
| SEQ ID NO: 4 | Nucleotide sequence of H7 regulatory region | 8 |
| SEQ ID NO: 5 | Nucleotide sequence of H11 regulatory region | 9 |
| SEQ ID NO: 6 | Nucleotide sequence of H12 regulatory region | 10 |
| SEQ ID NO: 7 | Nucleotide sequence of genomic H7 | 8 |
| SEQ ID NO: 8 | Nucleotide sequence of genomic H11 | 9 |
| SEQ ID NO: 9 | Nucleotide sequence of genomic H12 | 10 |
| SEQ ID NO: 10 | Amino acid sequence encoded by H7 coding region | 8 |
| SEQ ID NO: 11 | Amino acid sequence encoded by H12 coding region | 10 |
| SEQ ID NO: 12 | Nucleotide sequence of PCR-Select cDNA synthesis primer | 2 |
| SEQ ID NO: 13 | Nucleotide sequence of Adaptor 1 | 2 |
| SEQ ID NO: 14 | Nucleotide sequence of Adaptor 2R | 2 |
| SEQ ID NO: 15 | Nucleotide sequence of PCR primer 1 | 2 |
| SEQ ID NO: 16 | Nucleotdie sequence of nested PCR primer 1 | 2 |
| SEQ ID NO: 18 | Nucleotide sequence of complement (partial) | 2 |
| SEQ ID NO: 19 | Nucleotide sequence of complement (partial) | 2 |
| SEQ ID NO: 17 | Nucleotdie sequence of nested PCR primer 2R | 2 |

All citations are herein incorporated by reference.

The present invention has been described with regard to preferred embodiments. However, it will be obvious to persons skilled in the art that a number of variations and modifications can be made without departing from the scope of the invention as described herein.

What is claimed is:

1. An isolated harvest-inducible regulatory element comprising the nucleotide sequence of SEQ ID NO:4, wherein the regulatory element exhibits harvest-inducible activity.

2. A construct comprising said harvest-inducible regulatory element of claim 1, operably linked with a heterologous coding sequence of interest and a terminator region.

3. A construct comprising a heterologous coding sequence operably linked to the harvest-inducible regulatory element of claim 1, the harvest-inducible regulatory element further comprising a nucleotide sequence encoding a harvest-inducible protein.

4. A vector comprising the DNA construct of claim 2.

5. A vector comprising the DNA construct of claim 3.

6. A plant, plant tissue, plant seed, plant cell, or progeny therefrom, comprising the construct of claim 2.

7. A plant, plant tissue, plant seed, plant cell, or progeny therefrom, comprising the construct of claim 3.

8. The plant, plant tissue, plant seed, plant cell, or progeny therefrom according to claim 6, wherein the plant, plant tissue, plant seed, plant cell, or progeny therefrom is selected from the group consisting of potato, tomato, canola, corn, soybean, alfalfa, pea, lentil, forage legumes, clover, trefoil, forage grasses timothy, ryegrass, brome grass, fescue, cereal grasses, barley, wheat, sudan grass, and sorghum.

9. The plant, plant tissue, plant seed, plant cell, or progeny therefrom according to claim 7, wherein the plant, plant tissue, plant seed, plant cell, or progeny therefrom is selected from the group consisting of potato, tomato, canola, corn, soybean, alfalfa, pea, lentil, forage legumes, clover, trefoil, forage grasses, timothy, ryegrass, brome grass, fescue, cereal grasses, barley, wheat, sudan grass, and sorghum.

* * * * *

SEQUENCE LISTING

```
<160> NUMBER OF SEQ ID NOS: 19

<210> SEQ ID NO 1
<211> LENGTH: 474
<212> TYPE: DNA
<213> ORGANISM: Medicago sativa
<220> FEATURE:
<223> OTHER INFORMATION: Nucleotide sequence of H7 coding region

<400> SEQUENCE: 1
atgggtgttt tactttcaa tgatgaacat gtctcaaccg tggctccagc taaactctac      60
```

```
aaggctcttg caaaagatgc tgatgaaatc gtcccaaagg tgatttctgc tgcccaaagt    120
gttgaaattg ttgaaggaaa tggaggaccc ggaactatta agaagctatc cattgttgaa    180
gatggcaaaa ccaactttgt gctacacaaa ttagattcag tggatgaggc aaactttgga    240
tataactaca gcttagtggg aggaacaggg ttggatgaaa gtttagagaa agttgaattt    300
gagacaaaaa ttgttgctgg ctctgatggt ggatccattg ttaagatttc agtgaaatac    360
cataccaaag gtgatgcaac tctatctgaa gcagtacgtg aggagactaa ggccaaagga    420
actggactta tcaaggccat tgagggctac gttttagcaa accctaatta ctag          474

<210> SEQ ID NO 2
<211> LENGTH: 678
<212> TYPE: DNA
<213> ORGANISM: Medicago sativa
<220> FEATURE:
<223> OTHER INFORMATION: Nucleotide sequence of H11 coding region

<400> SEQUENCE: 2
atggcctcca cactcagtct tgtcaagctt cccattcttt caagcatcaa gacacgccaa     60
tcaacctcaa aacatgttgt tccacttcca tccaaattca atattgtccc tcccacccca    120
ctaaagtttt cattagatca tcaaattaat atcaaacaaa cttctcttct atccctcaca    180
gcaatcacat ttccattctt attggatacc aaagagtttg gatatttga aggaagaaca    240 tttgctctca ttcaccccat tgtgttgggg ggtttgttct tctatactct atatgctggc    300
tatttggggt ggcaatggcg ccgagttagg actattcaaa atgatattaa tgagctcaag    360
aaacaactca aacctgcacc ggtcgcccct gatggtaaag cacttgaaac ttcaccgcca    420
tcacctgttg aacttcaaat ccagaaactt actgaggaga ggaaagagct tatcaaaggt    480
tcatacaggg ataaacactt taatgctgga tccatacttc taggatttgg tgtctttgag    540
gctgttggtg tgaggactca acacatggtt aaggacagga aagctatttc caggtccaca    600
tttatttgca ggagcaggca ttaccgtctt atgggcactg gcagcagctc tagtaccacc    660
gatgcagaaa ggcagtga                                                  678

<210> SEQ ID NO 3
<211> LENGTH: 744
<212> TYPE: DNA
<213> ORGANISM: Medicago sativa
<220> FEATURE:
<223> OTHER INFORMATION: Nucleotide sequence of H12 coding region

<400> SEQUENCE: 3
atggcaacca acgaagatca aaagcaaact gaatctggaa gacatcaaga agttggtcac     60
aagagtcttt tacaaagtga tgctctttac cagtatattc tagagaccag tgtcttccca    120
agagaacatg aagccatgaa agagttgaga gaggtcacag caaaacaccc atggaacatc    180 atgacaaccct ctgcagatga aggacaattt ttgagcatgc tccttaaact tatcaatgct    240
aagaatacca tggaaattgg tgtctacact ggctactccc tccttgccac tgccctagct    300
attcctgaag atggaaagat tttggctatg acattaaca agaaaattta cgaattgggt    360
ctacctgtaa ttaaaaaagc tggtgttgat cacaaaattg atttcagaga aggtccagct    420
cttccagttc ttgatgaaat gatcaaagac gaaaagaatc atggtagcta cgatttcatt    480
tttgtggatg ctgacaaaga caattacctc aactaccata gaggttaat tgatcttgtt    540 aaagtgggag gtgtgatcgg gtacgacaac accttatgga atggatctgt ggttgcaccc    600
```

```
cctgatgctc cattgaggaa gtatgttagg tactatagag attttgtttt ggagcttaac    660
aaggctttgg ctgtggaccc taggattgaa atatgtatgc ttcctgttgg tgatggaatc    720
actatctgcc gtaggatcaa gtaa                                            744
```

<210> SEQ ID NO 4
<211> LENGTH: 634
<212> TYPE: DNA
<213> ORGANISM: Medicago sativa
<220> FEATURE:
<223> OTHER INFORMATION: Nucleotide sequence of H7 regulatory region

<400> SEQUENCE: 4

```
acgcgtggtc gacggcccgg gctggtacta agtattact attaccaaat ttttaggacc      60
ccacccatga caccattgct atatttcaat ttgggaaaat attgctataa agttactgta    120
gtaactttta gaagaaggtt ttttttttaa ggattttaga ggaaggttag caacacacat    180
gcactttaaa tatacatttt ttcttataaa gtttttgtat cgagttgaga aatcatatat    240
atactcataa atcatgtgga tttcatataa tttaatagaa cacataaatt ttaaccgaga    300
aataaagtgt tgcaaatata tgttaaaaga gtacgttgtt aacattattt taatttcttt    360
tattcaatcc acactttgag tcatggactg ctatactaat tcattttgtt tttcgcaacc    420
taattagaga ttgtccagat acaaagagga gtaacctaat aaataaatat taaaatattc    480
accaacggcc tcagtaagct acttgagcta acaatgaga tttccaaata aggtaggtcc     540
ttcccaagtt ctataaatag catccctcac catgtcataa accgcatcac aagttatata    600
ctgtattcat actatacact tatcctttca ttta                                 634
```

<210> SEQ ID NO 5
<211> LENGTH: 438
<212> TYPE: DNA
<213> ORGANISM: Medicago sativa
<220> FEATURE:
<223> OTHER INFORMATION: Nucleotide sequence of H11 regulatory region
<220> FEATURE:
<221> NAME/KEY: misc_feature
<222> LOCATION: (1)..(438)
<223> OTHER INFORMATION: where "n" is a or g or c or t or other

<400> SEQUENCE: 5

```
cagaaccccg anaggctggt gctagtatgg cttcgttgta atacgactca ctatagggcg     60
cgcgtggtcg acggcccggg ctggtatcag cgagtaacga ttcatcatat ctcacactag    120
ggatgaatga tttattattg agtttatgaa tttgaactat tacttctaat ttctaaatga    180
agacatttaa gtaaaagatt aaaatattct agtttcaaat attttggatt ttagaattta    240
aatttaatct ttaaaaaaaa attaaattta agaagataa aaagggagaa ataaaataga    300
tgaatataat ttgtaaacat gaagaccta tctccagtaa aaaacatat ggaccttatc     360 tttttgaggt aggaaggatc tacgcgggga acctcttcct gactgtgaac cccgtatgca    420
gaggcagaga cagagagt                                                   438
```

<210> SEQ ID NO 6
<211> LENGTH: 936
<212> TYPE: DNA
<213> ORGANISM: Medicago sativa
<220> FEATURE:
<223> OTHER INFORMATION: Nucleotide sequence of H12 regulatory region

<400> SEQUENCE: 6

```
aaatacaaag gtgaccttat tttgcaaata atccatgcat ggaaatgcat catccttttg     60
```

```
aaaatgggtt tatctgaatt cttaagttac gtgaaaattt aatacatttc attttagata    120
aatttattat taaaattcac acttagatgg cctaaaaatt aacacttatt tttaacaatt    180
caaataaaat atacgacgaa atgagtgtaa tttagttggt taagcatcgt caaagcttgg    240
agagaaagat catagtttga tctttgaaaa ctatactatt gaaaagggtg aagatatcta    300
acctccaaca aaatttattt gatagtcgat tcaaattatc aaaatttgga aaatattttg    360
taaattgtta agttgggaaa aatatgttaa ttttcaaatt accatttgca cattttccta    420
atctcaaatc acatttaagg gatgttgact actttcgttt tgtacaaatc tttacaattt    480
taacatttat aaaatgtgtt ttggtagata aaaagtgtga gtattcttta taagagattg    540 tgttttctt ttgttttaac ttataaaata aatatatatt ttattttatt ttaacgtgag    600
attgtaagaa ttcattataa gattatgtca ttccctcaaa agaaaattag atgatgtcat    660
tttcataact cattttctat aaatacagaa aatcctcaaa aatgaaaaac ctcggtcaaa    720
aaataaaaga aaaacatcaa tagtggactg gcccacactc attgctttgc tttagtatga    780
gaaagtagac ctcaccaacc acgaaccgga cgccgaccgg ttcaaccaaa catcacacca    840 atttttcctaa accataccgg ttttttccctc ccttatataa ccatcctctc ccctcttctc    900
taaccaagct tcattcaact cttcaacaca tatcag                             936

<210> SEQ ID NO 7
<211> LENGTH: 1424
<212> TYPE: DNA
<213> ORGANISM: Medicago sativa
<220> FEATURE:
<223> OTHER INFORMATION: Nucleotide sequence of genomic H7

<400> SEQUENCE: 7
acgcgtggtc gacggcccgg gctggtacta aagtattact attaccaaat ttttaggacc     60
ccacccatga caccattgct atatttcaat ttgggaaaat attgctataa agttactgta    120 gtaacttta gaagaaggtt ttttttttaa ggatttttaga ggaaggttag caacacacat    180
gcactttaaa tatacatttt ttcttataaa gttttttgtat cgagttgaga aatcatatat    240
atactcataa atcatgtgga tttcatataa tttaatagaa cacataaaatt ttaaccgaga    300 aataaagtgt tgcaaatata tgttaaaaga gtacgttgtt aacattattt taatttcttt    360
tattcaatcc acactttgag tcatggactg ctatactaat tcattttgtt tttcgcaacc    420
taattagaga ttgtccagat acaaagagga gtaacctaat aaataaatat taaaatattc    480
accaacggcc tcagtaagct acttgagcta acaatgaga tttccaaata aggtaggtcc    540
ttcccaagtt ctataaatag catccctcac catgtcataa accgcatcac aagttatata    600
ctgtattcat actatacact tatcctttca tttacttctt gcatattgat ccttgttatc    660
ttgatatata tatcatgggt gttttttactt tcaatgatga acatgtctca accgtggctc    720
cagctaaact ctacaaggct cttgcaaaag atgctgatga aatcgtccca aaggtgattt    780
ctgctgccca aagtgttgaa attgttgaag gaaatggagg acccggaact attaagaagc    840
tatccattgt tgaagatggc aaaaccaact tgtgctaca caaattagat tcagtggatg    900
aggcaaactt tggatataac tacagcttag tgggaggaac agggttggat gaaagtttag    960
agaaagttga atttgagaca aaaattgttg ctggctctga tggtggatcc attgttaaga   1020
tttcagtgaa ataccatacc aaaggtgatg caactctatc tgaagcagta cgtgaggaga   1080
ctaaggccaa aggaactgga cttatcaagg ccattgaggg ctacgtttta gcaaacccta   1140
```

-continued

| | |
|---|---|
| attactagcc aattaaaccc tattgaggac tttaatttgg gttgtgttgt ttcatgcgaa | 1200 |
| taataattaa agtttatgat gcggttgaag tgtgttgagt atacatcaag gtctttggct | 1260 |
| cgtacatgtg tgttggcttt gttggatgtt gtgaggtttg agtgctattt tgggtgttta | 1320 |
| aaaacaaaaa cctatgttgt gttggtgata aggttttgca ccatctgtat tatgcaataa | 1380 |
| ataatgcaaa agaatttat cgcgaaaaaa aaaaaaaaa aaaa | 1424 |

<210> SEQ ID NO 8
<211> LENGTH: 1482
<212> TYPE: DNA
<213> ORGANISM: Medicago sativa
<220> FEATURE:
<223> OTHER INFORMATION: Nucleotide sequence of genomic H11
<220> FEATURE:
<221> NAME/KEY: misc_feature
<222> LOCATION: (1)..(1482)
<223> OTHER INFORMATION: Where n is a or g or c or t or other

<400> SEQUENCE: 8

| | |
|---|---|
| cagaaccccg anaggctggt gctagtatgg cttcgttgta atacgactca ctatagggcg | 60 |
| cgcgtggtcg acggcccggg ctggtatcag cgagtaacga ttcatcatat ctcacactag | 120 |
| ggatgaatga tttattattg agtttatgaa tttgaactat tacttctaat ttctaaatga | 180 |
| agacatttaa gtaaaagatt aaaatattct agtttcaaat attttggatt ttagaattta | 240 |
| aatttaatct ttaaaaaaaa attaaattta agaagataa aagggagaa ataaaataga | 300 |
| tgaatataat ttgtaaacat gaagaccta tctccagtaa aaaacatat ggaccttatc | 360 |
| tttttgaggt aggaaggatc tacgcgggga acctcttcct gactgtgaac cccgtatgca | 420 |
| gaggcagaga cagagagtat ggcctccaca ctcagtcttg tcaagcttcc cattctttca | 480 |
| agcatcaaga cacgccaatc aacctcaaaa catgttgttc cacttccatc caaattcaat | 540 |
| attgtccctc ccacccact aaagttttca ttagatcatc aaattaatat caaacaaact | 600 |
| tctcttctat ccctcacagc aatcacattt ccattcttat tggataccaa ggcaagcaag | 660 |
| caagcaagca tcctattcta ttctattctt tcatccatat ctttactctt ttgttttcta | 720 |
| accaatccat gatatgaatg ttgttgaaac aggatgcact tgctgttggt ggagagtttg | 780 |
| ggatatttga aggaagaaca tttgctctca ttcaccccat tgtgttgggt ggttgttct | 840 |
| tctatactct atatgctggc tatttggggt ggcaatggcg ccgagttagg actattcaaa | 900 |
| atgatattaa tgagctcaag aaacaactca aacctgcacc ggtcgcccct gatggtaaag | 960 |
| cacttgaaac ttcaccgcca tcacctgttg aacttcaaat ccagaaactt actgaggaga | 1020 |
| ggaaagagct tatcaaaggt tcatacaggg ataaacactt taatgctgga tccatacttc | 1080 |
| taggatttgg tgtctttgag gctgttggtg tgaggactca acacatggtt aaggacagga | 1140 |
| aagctatttc caggtccaca tttatttgca ggagcaggca ttaccgtctt atgggcactg | 1200 |
| gcagcagctc tagtaccacc gatgcagaaa ggcagtgaaa cagccagaaa tcttcacatt | 1260 |
| gctctgaata cattgaatgt tcttctcttt gtgtggcaga ttcccactgg acttgatatt | 1320 |
| gtatggaaag tgtttgagtt cacaaaaatgg ccttgaatgt atgattctca tatgtaagta | 1380 |
| agttcccagg tattttactt tcaaatcagt atttggcaat atcaataaat gcaaaatttg | 1440 |
| ctattctgca ttttcaaaaa aaaaaaaaaa aaaaaaaaaa aa | 1482 |

<210> SEQ ID NO 9
<211> LENGTH: 1906
<212> TYPE: DNA
<213> ORGANISM: Medicago sativa -continued
<220> FEATURE:
<223> OTHER INFORMATION: Nucleotide sequence of genomic H12

<400> SEQUENCE: 9

```
aaatacaaag gtgaccttat tttgcaaata atccatgcat ggaaatgcat catccttttg     60
aaaatgggtt tatctgaatt cttaagttac gtgaaaattt aatacatttc attttagata    120
aatttattat taaaattcac acttagatgg cctaaaaatt aacacttatt tttaacaatt    180
caaataaaat atacgacgaa atgagtgtaa tttagttggt taagcatcgt caaagcttgg    240
agagaaagat catagtttga tctttgaaaa ctatactatt gaaaagggtg aagatatcta    300
acctccaaca aaatttattt gatagtcgat tcaaattatc aaaatttgga aaatattttg    360
taaattgtta agttgggaaa aatatgttaa ttttcaaatt accatttgca catttttcta    420
atctcaaatc acatttaagg gatgttgact actttcgttt tgtacaaatc tttacaattt    480
taacatttat aaaatgtgtt ttggtagata aaaagtgtga gtattcttta taagagattg    540
tgtttttctt ttgttttaac ttataaaata aatatatatt ttattttatt ttaacgtgag    600
attgtaagaa ttcattataa gattatgtca ttccctcaaa agaaaattag atgatgtcat    660
tttcataact cattttctat aaatacagaa aatcctcaaa aatgaaaaac ctcggtcaaa    720
aaataaaaga aaaacatcaa tagtggactg gcccacactc attgctttgc tttagtatga    780
gaaagtagac ctcaccaacc acgaaccgga cgccgaccgg ttcaaccaaa catcacacca    840
attttcctaa accataccgg tttttccctc ccttatataa ccatcctctc ccctcttctc    900
taaccaagct tcattcaact cttcaacaca tatcagaaac agaaaaaaga agcaaaacat    960
tccaagaatt taacaatggc aaccaacgaa gatcaaaagc aaactgaatc tggaagacat   1020
caagaagttg gtcacaagag tcttttacaa agtgatgctc tttaccagta tattctagag   1080
accagtgtct tcccaagaga acatgaagcc atgaaagagt tgagagaggt cacagcaaaa   1140
cacccatgga acatcatgac aacctctgca gatgaaggac aatttttgag catgctcctt   1200
aaacttatca atgctaagaa taccatggaa attggtgtct acactggcta ctccctcctt   1260
gccactgccc tagctattcc tgaagatgga aagattttgg ctatggacat taacaaagaa   1320
aattacgaat tgggtctacc tgtaattaaa aaagctggtg ttgatcacaa aattgatttc   1380
agagaaggtc cagctcttcc agttcttgat gaaatgatca aagacgaaaa gaatcatggt   1440
agctacgatt tcatttttgt ggatgctgac aaagacaatt acctcaacta ccataagagg   1500
ttaattgatc ttgttaaagt gggaggtgtg atcgggtacg acaacacctt atggaatgga   1560
tctgtggttg cacccccctga tgctccattg aggaagtatg ttaggtacta tagagatttt   1620
gttttggagc ttaacaaggc tttggctgtg gaccctagga ttgaaatatg tatgcttcct   1680
gttggtgatg gaatcactat ctgccgtagg atcaagtaat tggtttgcat gtgcactata   1740
tcatgtaatg cactgctcca cattattgat cattattgtg tggaagctac agagcattta   1800
aaagtcttca agccttcttg tcttttgtta tttttcttca acatatttgt ggttgtaatt   1860
ttctcttgtc attgatattg aaacttcgaa taattgaaag ttatat                  1906
```

<210> SEQ ID NO 10
<211> LENGTH: 157
<212> TYPE: PRT
<213> ORGANISM: Medicago sativa
<220> FEATURE:
<223> OTHER INFORMATION: Amino acid sequence encoded by H7 coding region

<400> SEQUENCE: 10

```
Met Gly Val Phe Thr Phe Asn Asp Glu His Val Ser Thr Val Ala Pro
1               5                   10                  15

Ala Lys Leu Tyr Lys Ala Leu Ala Lys Asp Ala Asp Glu Ile Val Pro
            20                  25                  30

Lys Val Ile Ser Ala Ala Gln Ser Val Glu Ile Val Glu Gly Asn Gly
        35                  40                  45

Gly Pro Gly Thr Ile Lys Lys Leu Ser Ile Val Glu Asp Gly Lys Thr
    50                  55                  60

Asn Phe Val Leu His Lys Leu Asp Ser Val Asp Glu Ala Asn Phe Gly
65                  70                  75                  80

Tyr Asn Tyr Ser Leu Val Gly Gly Thr Gly Leu Asp Glu Ser Leu Glu
                85                  90                  95

Lys Val Glu Phe Glu Thr Lys Ile Val Ala Gly Ser Asp Gly Gly Ser
            100                 105                 110

Ile Val Lys Ile Ser Val Lys Tyr His Thr Lys Gly Asp Ala Thr Leu
        115                 120                 125

Ser Glu Ala Val Arg Glu Glu Thr Lys Ala Lys Gly Thr Gly Leu Ile
    130                 135                 140

Lys Ala Ile Glu Gly Tyr Val Leu Ala Asn Pro Asn Tyr
145                 150                 155

<210> SEQ ID NO 11
<211> LENGTH: 247
<212> TYPE: PRT
<213> ORGANISM: Medicago sativa
<220> FEATURE:
<223> OTHER INFORMATION: Amino acid sequence encoded by H12 coding
      region

<400> SEQUENCE: 11

Met Ala Thr Asn Glu Asp Gln Lys Gln Thr Glu Ser Gly Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Phe Pro Arg Glu His Glu Ala Met Lys Glu
        35                  40                  45

Leu Arg Glu Val Thr Ala Lys His Pro Trp Asn Ile Met Thr Thr Ser
    50                  55                  60

Ala Asp Glu Gly Gln Phe Leu Ser Met Leu Leu Lys Leu Ile Asn Ala
65                  70                  75                  80

Lys Asn Thr Met Glu Ile Gly Val Tyr Thr Gly Tyr Ser Leu Leu Ala
                85                  90                  95

Thr Ala Leu Ala Ile Pro Glu Asp Gly Lys Ile Leu Ala Met Asp Ile
            100                 105                 110

Asn Lys Glu Asn Tyr Glu Leu Gly Leu Pro Val Ile Lys Lys Ala Gly
        115                 120                 125

Val Asp His Lys Ile Asp Phe Arg Glu Gly Pro Ala Leu Pro Val Leu
    130                 135                 140

Asp Glu Met Ile Lys Asp Glu Lys Asn His Gly Ser Tyr Asp Phe Ile
145                 150                 155                 160

Phe Val Asp Ala Asp Lys Asp Asn Tyr Leu Asn Tyr His Lys Arg Leu
                165                 170                 175

Ile Asp Leu Val Lys Val Gly Gly Val Ile Gly Tyr Asp Asn Thr Leu
            180                 185                 190

Trp Asn Gly Ser Val Val Ala Pro Pro Asp Ala Pro Leu Arg Lys Tyr
        195                 200                 205
```

Val Arg Tyr Tyr Arg Asp Phe Val Leu Glu Leu Asn Lys Ala Leu Ala
    210                 215                 220

Val Asp Pro Arg Ile Glu Ile Cys Met Leu Pro Val Gly Asp Gly Ile
225                 230                 235                 240

Thr Ile Cys Arg Arg Ile Lys
                245

<210> SEQ ID NO 12
<211> LENGTH: 44
<212> TYPE: DNA
<213> ORGANISM: Artificial Sequence
<220> FEATURE:
<223> OTHER INFORMATION: Nucleotide sequence of PCR-Select cDNA
      synthesis primer; see FIG. 2
<220> FEATURE:
<221> NAME/KEY: misc_feature
<222> LOCATION: (1)..(44)
<223> OTHER INFORMATION: where n is a or g or c or t or other

<400> SEQUENCE: 12
ttttgtacaa gctttttttt tttttttttt tttttttttt ttnn            44

<210> SEQ ID NO 13
<211> LENGTH: 44
<212> TYPE: DNA
<213> ORGANISM: Artificial Sequence
<220> FEATURE:
<223> OTHER INFORMATION: Nucleotide sequence of Adaptor 1; see FIG. 2

<400> SEQUENCE: 13
ctaatacgac tcactatagg gctcgagcgg ccgcccgggc aggt            44

<210> SEQ ID NO 14
<211> LENGTH: 42
<212> TYPE: DNA
<213> ORGANISM: Artificial Sequence
<220> FEATURE:
<223> OTHER INFORMATION: Nucleotide sequence of Adaptor 2R; see FIG. 2

<400> SEQUENCE: 14
ctaatacgac tcactatagg gcagcgtggt cgcggccgag gt              42

<210> SEQ ID NO 15
<211> LENGTH: 22
<212> TYPE: DNA
<213> ORGANISM: Artificial Sequence
<220> FEATURE:
<223> OTHER INFORMATION: Nucleotide sequence of PCR primer 1; see FIG. 2

<400> SEQUENCE: 15
ctaatacgac tcactatagg gc                                    22

<210> SEQ ID NO 16
<211> LENGTH: 19
<212> TYPE: DNA
<213> ORGANISM: Artificial Sequence
<220> FEATURE:
<223> OTHER INFORMATION: Nucleotide sequence of nested PCR primer 1; see
      FIG. 2

<400> SEQUENCE: 16
tcgagcggcc gcccgggca                                        19

<210> SEQ ID NO 17
<211> LENGTH: 20

```
<212> TYPE: DNA
<213> ORGANISM: Artificial Sequence
<220> FEATURE:
<223> OTHER INFORMATION: Nucleotide sequence of nested PCR primer 2R;
      see FIG. 2

<400> SEQUENCE: 17
agcgtggtcg cggccgaggt                                                  20

<210> SEQ ID NO 18
<211> LENGTH: 10
<212> TYPE: DNA
<213> ORGANISM: Artificial Sequence
<220> FEATURE:
<223> OTHER INFORMATION: Nucleotide sequence of complement (partial);
      see FIG. 2

<400> SEQUENCE: 18
ggcccgtcca                                                             10

<210> SEQ ID NO 19
<211> LENGTH: 10
<212> TYPE: DNA
<213> ORGANISM: Artificial Sequence
<220> FEATURE:
<223> OTHER INFORMATION: Nucleotide sequence of complement (partial);
      see FIG. 2

<400> SEQUENCE: 19
gccggctcca                                                             10
```